United States Patent
Tan et al.

(10) Patent No.: US 8,603,009 B2
(45) Date of Patent: Dec. 10, 2013

(54) FLASHBACK BLOOD COLLECTION NEEDLE

(75) Inventors: Alvin Chee Leong Tan, Singapore (SG); Tiong Yee Sim, Johor (MY); Jon Yaohan Moh, Singapore (SG); William G. Saulenas, Wayne, NJ (US); Robert G. Ellis, Wayne, NJ (US); James C. Schneider, Wayne, NJ (US); Steven Mark White, Plymouth (GB)

(73) Assignee: Becton, Dickinson and Company, Franklin Lakes, NJ (US)

(*) Notice: Subject to any disclaimer, the term of this patent is extended or adjusted under 35 U.S.C. 154(b) by 228 days.

(21) Appl. No.: 13/018,740

(22) Filed: Feb. 1, 2011

(65) Prior Publication Data
US 2011/0178427 A1 Jul. 21, 2011

Related U.S. Application Data

(63) Continuation-in-part of application No. 12/206,273, filed on Sep. 8, 2008, and a continuation-in-part of application No. 12/044,354, filed on Mar. 7, 2008, now Pat. No. 7,766,879.

(51) Int. Cl.
*A61B 5/00* (2006.01)
*B65D 81/00* (2006.01)
*A61M 5/178* (2006.01)

(52) U.S. Cl.
USPC ..................... 600/573; 604/168.01

(58) Field of Classification Search
USPC .......... 600/573, 576–583; 604/122, 272, 164, 604/264, 168.01
See application file for complete search history.

(56) References Cited

U.S. PATENT DOCUMENTS

| | | |
|---|---|---|
| 4,106,497 A | 8/1978 | Percarpio |
| 4,207,870 A | 6/1980 | Eldridge |
| 4,305,406 A | 12/1981 | Megahed |
| 4,572,210 A | 2/1986 | McKinnon |
| 4,573,976 A | 3/1986 | Sampson et al. |
| 4,641,663 A | 2/1987 | Juhn |
| 4,795,443 A | 1/1989 | Permenter et al. |
| 4,840,619 A | 6/1989 | Hughes |
| 4,894,055 A | 1/1990 | Sudnak |
| 4,900,307 A | 2/1990 | Kulli |
| 4,994,046 A | 2/1991 | Wesson et al. |
| 5,015,241 A | 5/1991 | Feimer |

(Continued)

FOREIGN PATENT DOCUMENTS

| | | |
|---|---|---|
| EP | 0060385 A1 | 9/1982 |
| EP | 1579805 A1 | 9/2005 |

(Continued)

*Primary Examiner* — Brian Szmal
(74) *Attorney, Agent, or Firm* — The Webb Law Firm

(57) ABSTRACT

A needle assembly includes a transparent or translucent housing with a fluid inlet and outlet end, a flashback chamber, and a venting mechanism therebetween. The venting mechanism includes a blocking member to control the fluid flow in the venting mechanism so that it flows along the longest path through the vent. Substantially axially aligned inlet and outlet cannulas extend from the housing and communicate with the chamber. A sealable sleeve covers the external end of the outlet cannula. Relative volumes of the cannulas, the chamber, and the sleeve are selected to provide rapid reliable flashback indicative of venous entry with an internal vent positioned within the housing to divide the interior into first and second chambers, with the second chamber being adapted to maintain a negative pressure therein relative to the external environment so as to inhibit leakage of blood from the needle tip on withdrawal from the patient.

32 Claims, 27 Drawing Sheets

(56) References Cited

U.S. PATENT DOCUMENTS

| | | |
|---|---|---|
| 5,195,985 A | 3/1993 | Hall |
| 5,215,534 A | 6/1993 | De Harde et al. |
| 5,222,502 A | 6/1993 | Kurose |
| 5,242,417 A | 9/1993 | Paudler |
| 5,246,428 A | 9/1993 | Falknor |
| 5,256,153 A | 10/1993 | Hake |
| 5,295,970 A | 3/1994 | Clinton et al. |
| 5,303,713 A | 4/1994 | Kurose |
| 5,312,372 A | 5/1994 | DeHarde et al. |
| 5,336,199 A | 8/1994 | Castillo et al. |
| 5,348,544 A | 9/1994 | Sweeney et al. |
| 5,356,392 A | 10/1994 | Firth et al. |
| 5,411,492 A | 5/1995 | Sturman et al. |
| 5,439,449 A | 8/1995 | Mapes et al. |
| 5,466,223 A | 11/1995 | Bressler et al. |
| 5,501,675 A | 3/1996 | Erskine |
| 5,542,932 A | 8/1996 | Daugherty |
| 5,599,313 A | 2/1997 | Gyure et al. |
| 5,662,617 A | 9/1997 | Odell et al. |
| 5,665,075 A | 9/1997 | Gyure et al. |
| 5,672,161 A | 9/1997 | Allen et al. |
| 5,676,658 A | 10/1997 | Erskine |
| 5,702,369 A | 12/1997 | Mercereau |
| 5,704,920 A | 1/1998 | Gyure |
| 5,733,265 A | 3/1998 | Bachman et al. |
| 5,755,522 A | 5/1998 | Ito |
| 5,957,892 A | 9/1999 | Thorne |
| 5,984,899 A | 11/1999 | D'Alessio et al. |
| D422,700 S | 4/2000 | Crawford et al. |
| 6,149,629 A | 11/2000 | Wilson et al. |
| D442,280 S | 5/2001 | Crawford et al. |
| 6,224,576 B1 | 5/2001 | Thorne et al. |
| 6,254,575 B1 | 7/2001 | Thorne, Jr. et al. |
| 6,261,263 B1 | 7/2001 | Huet et al. |
| 6,298,541 B1 | 10/2001 | Newby et al. |
| 6,344,032 B1 | 2/2002 | Perez et al. |
| 6,436,086 B1 | 8/2002 | Newby et al. |
| 6,440,104 B1 | 8/2002 | Newby et al. |
| 6,524,277 B1 | 2/2003 | Chang |
| 6,533,760 B2 | 3/2003 | Leong |
| 6,592,556 B1 | 7/2003 | Thorne |
| 6,623,456 B1 | 9/2003 | Holdaway et al. |
| 6,635,032 B2 | 10/2003 | Ward, Jr. |
| 6,648,855 B2 | 11/2003 | Crawford et al. |
| 6,695,819 B2 | 2/2004 | Kobayashi |
| 6,699,217 B2 | 3/2004 | Bennett et al. |
| 6,712,792 B2 | 3/2004 | Leong |
| 6,780,169 B2 | 8/2004 | Crawford |
| 6,837,877 B2 | 1/2005 | Zurcher |
| 6,869,415 B2 | 3/2005 | Asbaghi |
| 6,984,223 B2 | 1/2006 | Newby et al. |
| 7,001,363 B2 | 2/2006 | Ferguson et al. |
| 7,128,726 B2 | 10/2006 | Crawford et al. |
| 7,147,624 B2 | 12/2006 | Hirsiger et al. |
| 7,160,267 B2 | 1/2007 | Brown |
| 7,163,526 B2 | 1/2007 | Leong et al. |
| 7,223,258 B2 | 5/2007 | Crawford |
| 7,226,432 B2 | 6/2007 | Brown |
| 7,396,343 B2 | 7/2008 | Brown |
| 7,428,773 B2 | 9/2008 | Newby et al. |
| 7,537,581 B2 | 5/2009 | Hwang |
| D604,836 S | 11/2009 | Crawford et al. |
| D604,837 S | 11/2009 | Crawford et al. |
| D604,838 S | 11/2009 | Crawford et al. |
| D604,839 S | 11/2009 | Crawford et al. |
| D605,287 S | 12/2009 | Crawford et al. |
| 7,766,879 B2 | 8/2010 | Tan et al. |
| 2002/0193748 A1 | 12/2002 | Cocker et al. |
| 2003/0093009 A1 | 5/2003 | Newby et al. |
| 2003/0105414 A1 | 6/2003 | Leong |
| 2003/0220614 A1 | 11/2003 | Crawford |
| 2003/0229315 A1 | 12/2003 | Leong et al. |
| 2004/0059302 A1 | 3/2004 | Crawford et al. |
| 2004/0092872 A1 | 5/2004 | Botich et al. |
| 2004/0193120 A1 | 9/2004 | Ferguson et al. |
| 2005/0004524 A1 | 1/2005 | Newby et al. |
| 2005/0065482 A1 | 3/2005 | Hauri et al. |
| 2005/0124944 A1 | 6/2005 | Hwang |
| 2005/0187493 A1 | 8/2005 | Swenson et al. |
| 2005/0245868 A1 | 11/2005 | Brown |
| 2005/0245869 A1 | 11/2005 | Brown |
| 2005/0245870 A1 | 11/2005 | Brown |
| 2005/0245879 A9 | 11/2005 | Crawford |
| 2005/0245885 A1 | 11/2005 | Brown |
| 2006/0036219 A1 | 2/2006 | Alvin |
| 2006/0224122 A1 | 10/2006 | Bosel et al. |
| 2007/0106220 A1 | 5/2007 | Brown |
| 2007/0106224 A1 | 5/2007 | Hwang |
| 2007/0167914 A1 | 7/2007 | Leong et al. |
| 2008/0086085 A1 | 4/2008 | Brown |
| 2008/0177202 A1 | 7/2008 | Brown |
| 2008/0319345 A1 | 12/2008 | Swenson |
| 2008/0319346 A1 | 12/2008 | Crawford et al. |
| 2009/0204026 A1 | 8/2009 | Crawford et al. |
| 2010/0262038 A1 | 10/2010 | Tan et al. |

FOREIGN PATENT DOCUMENTS

| | | | |
|---|---|---|---|
| EP | 1665986 | B1 | 6/2009 |
| JP | 57011661 | A | 1/1982 |
| JP | 57089869 | A | 6/1982 |
| JP | 6285172 | A | 10/1994 |
| JP | 2005176928 | | 7/2005 |
| JP | 2005349196 | | 12/2005 |
| WO | 9629107 | A1 | 9/1996 |
| WO | 2006022716 | A1 | 3/2006 |
| WO | 2009110922 | A1 | 9/2009 |

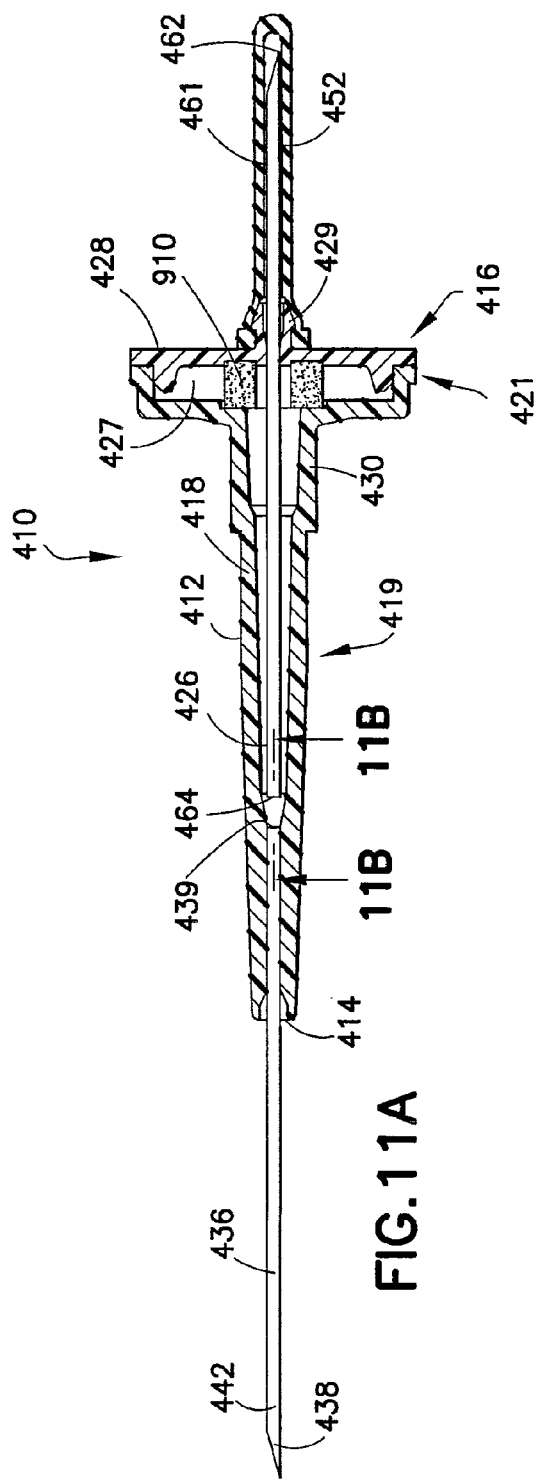
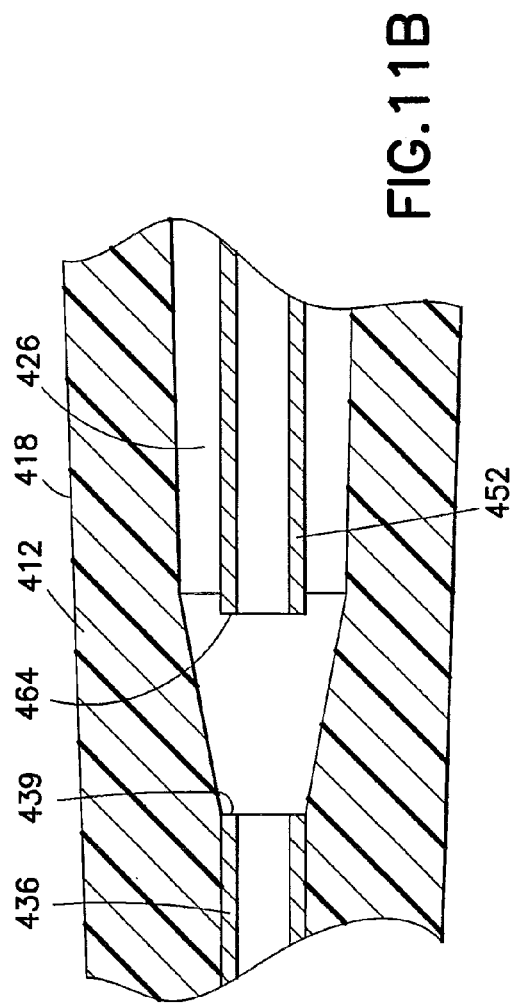
FIG.11A
FIG.11B

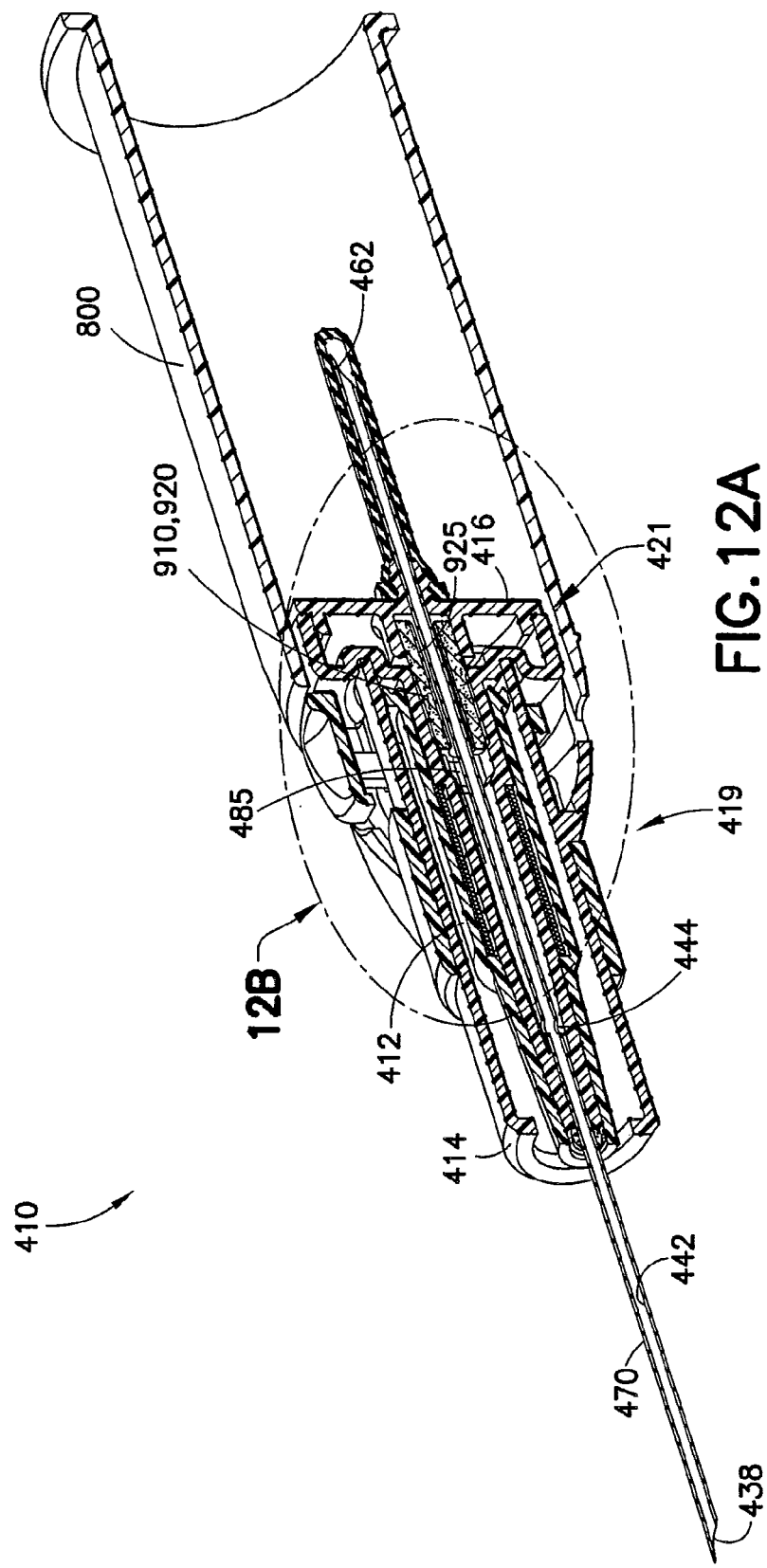

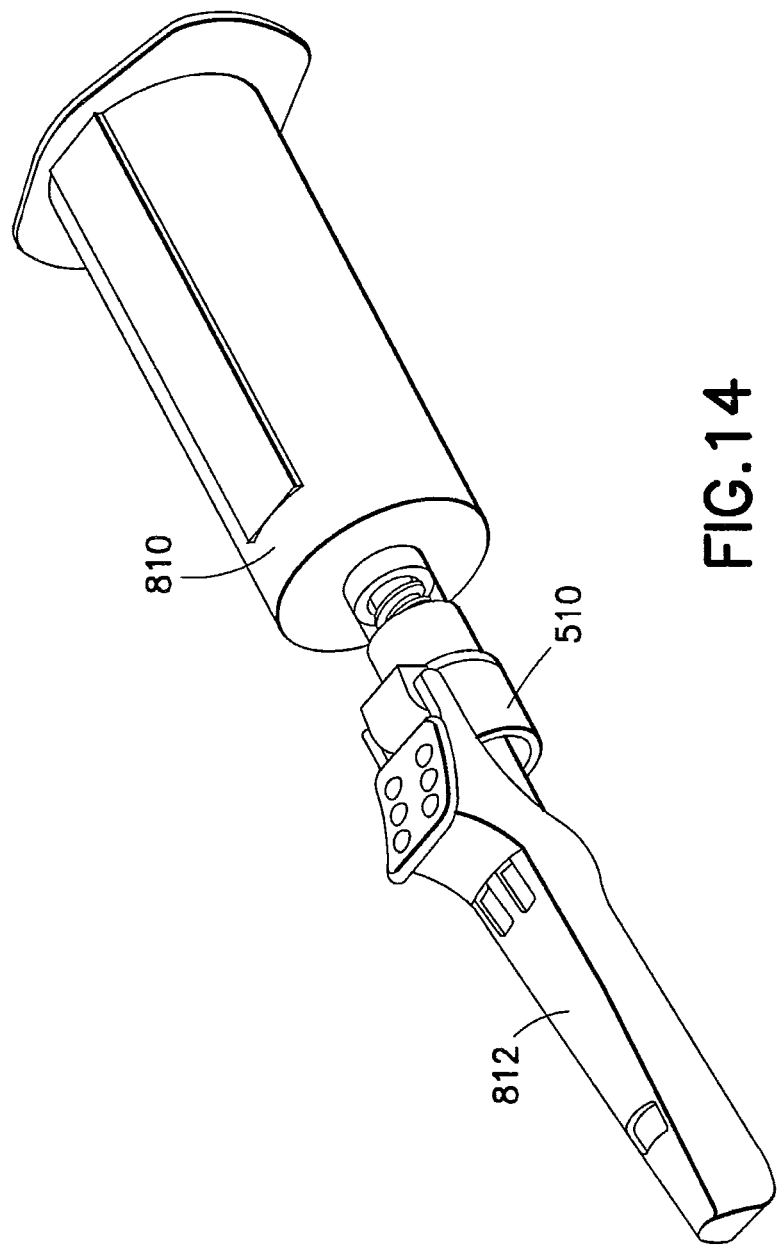

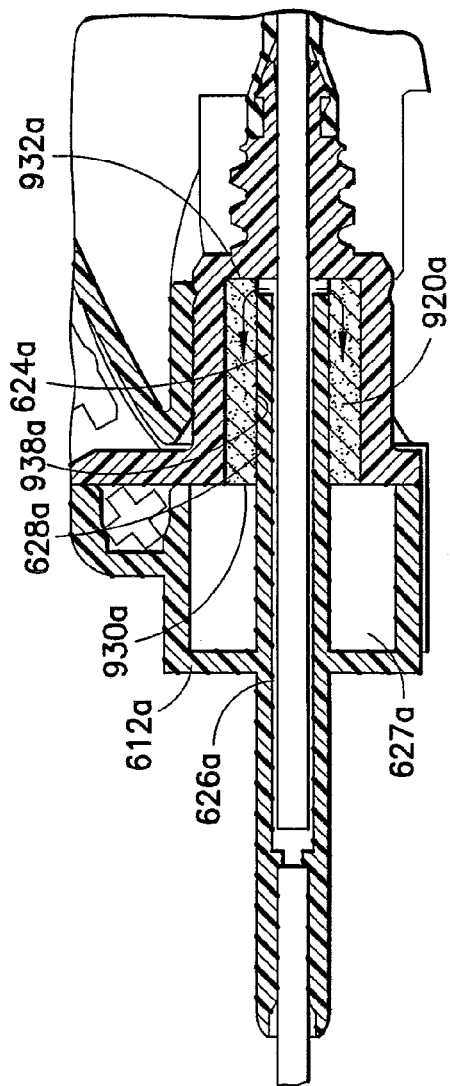
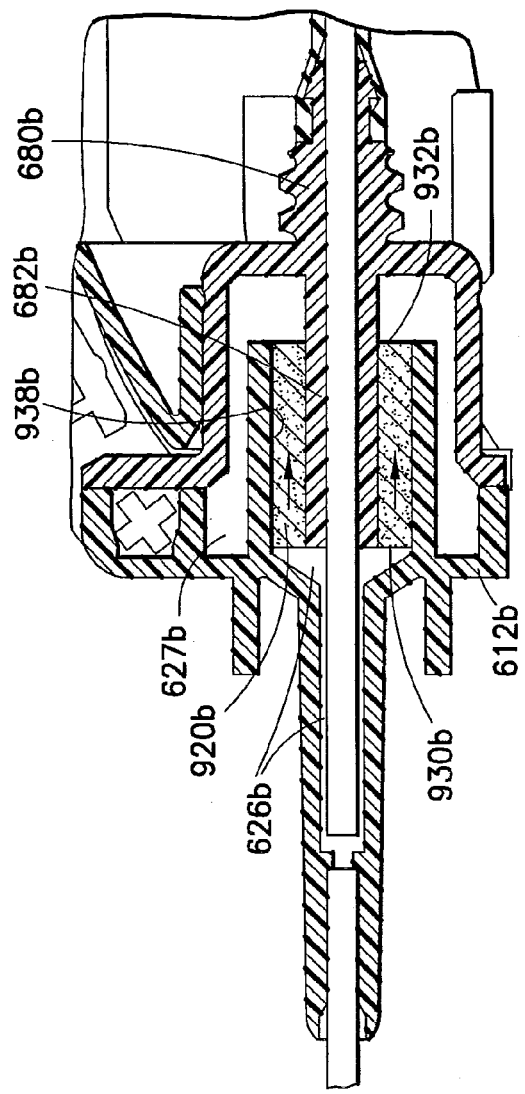

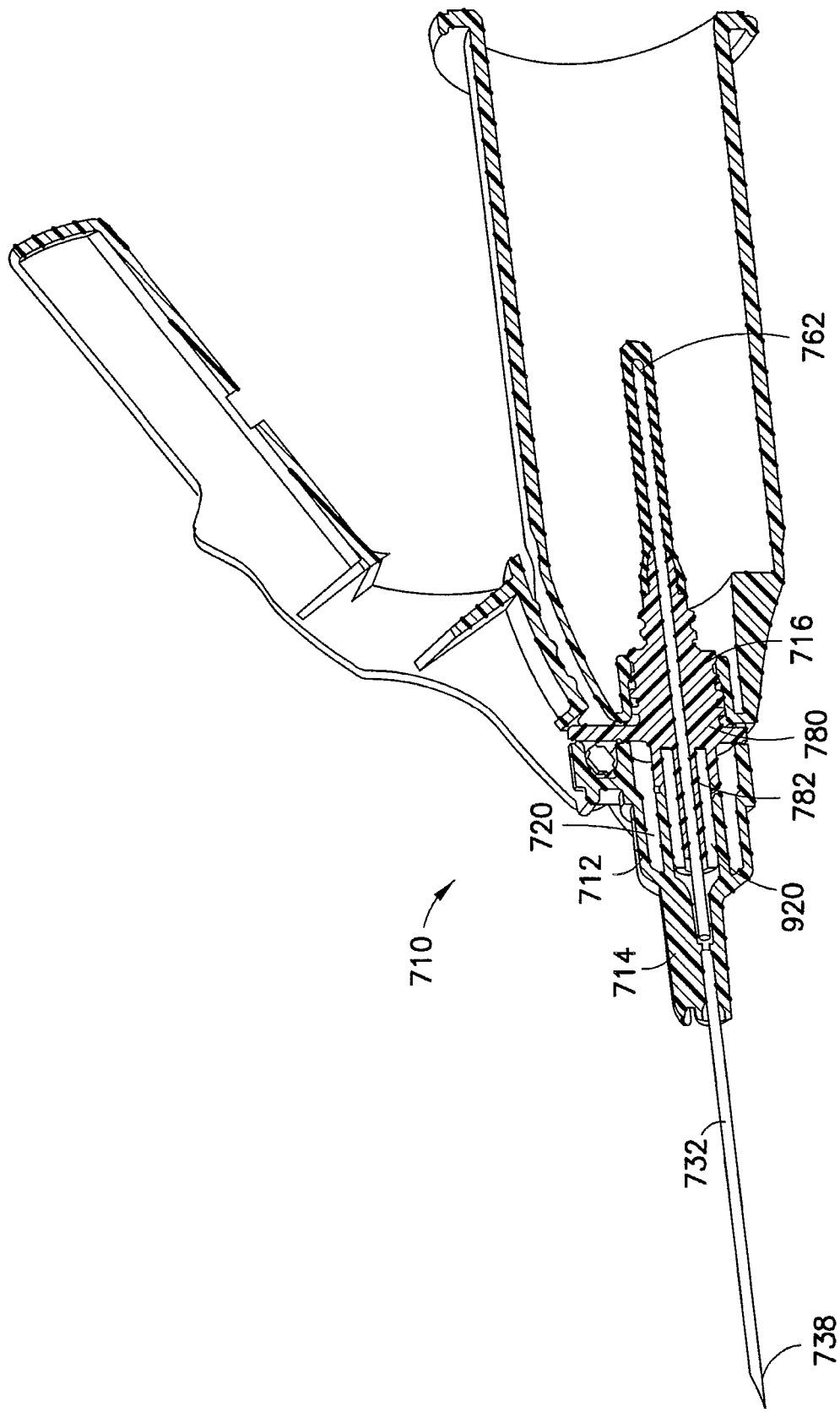

FLASHBACK BLOOD COLLECTION NEEDLE

The present application is a Continuation-in-Part application based upon U.S. application Ser. No. 12/206,273, filed Sep. 8, 2008, entitled "Flashback Blood Collection Needle" which is a Continuation-in-Part application based upon U.S. application Ser. No. 12/044,354 filed on Mar. 7, 2008, also entitled "Flashback Blood Collection Needle", the entire disclosures of each of which are herein incorporated by reference.

BACKGROUND OF THE INVENTION

1. Field of the Invention

The present invention relates to a device for collecting blood samples by performing venipuncture on a patient. More particularly, the present invention relates to a needle assembly for multiple sample blood collection that allows a phlebotomist to determine whether vein entry has occurred when collecting a blood sample from a patient into an evacuated blood collection tube.

2. Description of Related Art

Venipuncture is the primary method used for acquiring blood samples for laboratory testing. In performing venipuncture procedures, a phlebotomist must follow several steps simultaneously. Such steps include assessing the patient's overall physical and psychological condition so as to properly select a venipuncture site and technique. The phlebotomist must also select the proper corresponding equipment, perform the technique so as to control bleeding, and properly collect and identify fluid specimens for testing. The phlebotomist must ascertain all of these coinciding factors, as such factors may adversely affect the distension of the vein and the length of the venipuncture procedure.

Various venipuncture devices have been developed to address the above-described problems. These devices include products intended to assist the phlebotomist in confirming that vein entry has been made see e.g., U.S. Pat. Nos. 5,222,502 and 5,303,713. Such a device contains a needle assembly with a housing that defines a chamber therein. A single cannula pointed at both ends is affixed to the housing. The intravenous (IV) end of the cannula is adapted for penetration of a patient's vein. The non-patient end of the cannula has a sealable sleeve and is adapted for penetration of a penetrable stopper positioned within an evacuated container.

Upon vein entry with the intravenous end of the cannula, blood will flow through the cannula, into the sealable sleeve and into the housing chamber, which is clear or translucent for visualization ("flashback"). Once air is vented from the flashback chamber, the blood therein is pressurized each time the sealable sleeve is pushed toward the housing chamber upon activation of an evacuated container.

Due to the length of time between vein entry and flashback, the phlebotomist may erroneously believe that satisfactory vein entry has not been achieved since there is no immediate indication of vein entry in the see-through chamber. The phlebotomist may unnecessarily repeat the venipuncture procedure, requiring replacement of the evacuated container and/or the needle assembly itself. Such a repetitive process prolongs the physical and emotional discomfort endured by the patient. In such cases, a phlebotomist may use a blood collection set to provide some entry indication, and will then incur the cost of the blood collection set, as well as the cost of a discard tube.

It would therefore be desirable to provide an improved blood collection device that permits blood flow through a relatively short flow path directly into a flashback chamber, thereby providing immediate indication of successful vein entry.

SUMMARY OF THE INVENTION

The invention provides a needle assembly for the extraction of at least one fluid sample into an evacuated container for laboratory testing. The needle assembly provides a clear or translucent housing with sufficient dead space for blood to flow into a flashback chamber for visualization by the user to confirm successful vein entry, with an internal vent mechanism.

In one embodiment, the invention relates to a needle assembly comprising a housing defining a housing interior, a cannula having a patient puncture tip extending from a first end of the housing, and a non-patient puncture tip extending from a second end of the housing. The non-patient puncture tip and the patient puncture tip are in fluid communication with each other through the cannula, such that the sole communication path between the housing interior and the external environment is via the patient puncture tip. A porous vent is positioned within the housing interior to separate the housing interior into a first chamber and a second chamber, with the cannula being in fluid communication with the first chamber. The porous vent includes pores for passage of blood therethrough from the first chamber to the second chamber. The first chamber and the second chamber are configured such that upon insertion of the patient needle tip into a patient, blood flows through the cannula and into the first chamber without sealing the porous vent. At this point in the process, the blood "flashback" can be visualized in the first chamber. Upon application of an evacuated container to the non-patient puncture tip, blood is drawn from the first chamber and air is drawn from the second chamber, thereby establishing a negative pressure within the second chamber with respect to an external environment of the needle assembly. Blood can thereafter be drawn into the first chamber and through the porous vent, with a negative pressure maintained in the second chamber.

In one embodiment, the cannula includes a first end comprising the patient puncture tip and a second end comprising the non-patient puncture tip, with an opening between the first end and the second end providing fluid communication between the cannula and the first chamber of the housing. In an alternate embodiment, the cannula comprises a first cannula having a patient puncture tip, with the needle assembly further comprising a second cannula including the non-patient puncture tip, with the first cannula and the second cannula substantially axially aligned and separated by a gap in fluid communication with the first chamber of the housing. A sleeve may also extend about the non-patient puncture tip.

In one embodiment, the second chamber may include multiple interior regions in fluid communication, such as a first interior region and a second interior region. The first and second interior regions of the second chamber are in fluid communication with each other through the porous vent.

In a particular embodiment, the first end of the housing comprises an elongated longitudinal first portion having a first diameter and the second end of the housing comprises a second portion having a second diameter larger than the first diameter of the first portion. In such an embodiment, the porous vent may be positioned within the housing interior between the first portion having a first diameter and the second portion having a second diameter. Alternatively, the porous vent may be positioned within the housing interior at a location spanning the transition between the first diameter of the first portion and the second diameter of the second portion. In embodiments where the second chamber includes multiple interior regions, such as a first interior region and a second interior region, the first chamber may extend along a portion of the longitudinal first portion, with at least one of the interior regions, such as the second interior region of the second chamber extending longitudinally concentrically about the first chamber. In this manner, the external diameter, and thus the external profile of the needle assembly, can be decreased.

In yet a further embodiment, a method of preventing leakage, such as, for example, blood droplets, at the patient puncture tip in a needle assembly is provided. The method involves receiving blood through a patient puncture tip and into a first chamber of a needle assembly, with the needle assembly including a needle housing defining a housing interior; a cannula having the patient puncture tip extending from a first end of the needle housing; a non-patient puncture tip extending from a second end of the needle housing, the non-patient puncture tip and the patient puncture tip being in fluid communication with each other through the cannula; and a porous vent positioned within the housing interior and separating the housing interior into a first chamber and a second chamber. The cannula is in fluid communication with the first chamber such that the sole communication path between the housing interior and the external environment is via the patient puncture tip, and the porous vent includes pores for passage of blood therethrough from the first chamber into the second chamber. Fluid communication is established between the non-patient puncture tip and an evacuated collection container, such that blood contained within the first chamber is drawn into the evacuated collection container and air is drawn out of the second chamber through the porous vent. As such, a negative pressure is established within the second chamber relative to the external environment of the needle assembly, such that blood flows through the cannula into the first chamber and contacts the porous vent. Blood is then drawn through the pores of the porous vent toward the second chamber such that after removing the patient puncture tip from the vasculature of the patient any blood contained within the cannula is displaced away from the patient puncture tip toward the second chamber based upon the negative pressure established within the second chamber.

Additionally, a further step may include establishing fluid communication between the non-patient puncture tip and a second evacuated collection container prior to drawing blood through the patient puncture tip and through the cannula into the second evacuated collection container, followed by releasing the fluid communication between the non-patient puncture tip and the second evacuated collection container.

In yet a further embodiment, the invention is directed to a method of collecting a sample of blood from a patient into an evacuated blood collection tube using a blood collection assembly having a patient needle tip and a non-patient needle tip and a housing having a flashback visualization chamber. The method involves using a needle assembly comprising a housing having a porous vent positioned therein to separate an interior of the housing into a first chamber forming the flashback visualization chamber and a second chamber, the first chamber and second chamber being configured such that air is drawn out of the second chamber through the porous vent and into the evacuated blood collection tube along with the blood sample, thereby establishing a negative pressure within the second chamber. The negative pressure causes blood to be drawn into the first chamber and contact the porous vent, such that after the patient needle tip is removed from the patient, the negative pressure within the second chamber draws blood from the patient needle tip toward the second chamber, thereby preventing leakage of blood from the patient needle tip after removal from the patient.

In another embodiment, the invention is related to a needle assembly having a housing defining a housing interior wherein the housing comprises at least one cannula having a patient puncture tip extending from a first end of the housing and a non-patient puncture tip extending from a second end of the housing. The non-patient puncture tip and the patient puncture tip are in fluid communication with each other within the housing interior. The assembly also includes a porous vent positioned within the housing interior separating the housing interior into a first chamber and a second chamber within the housing interior. The porous vent includes pores for passage of fluid therethrough from the first chamber to the second chamber. The porous vent can comprise a tubular member including an axial bore which surrounds at least a portion of the at least one cannula. A blocking member is located adjacent to or within the axial bore of the porous vent and controls flow of the fluid through the vent such that the fluid flows along the longest path through the porous vent. This longest path depends upon the shape of the porous vent. In one embodiment wherein the porous vent is cylindrically or tubular shaped having a longer length than circumference, the flow can be in an axial direction along a longitudinal path through the porous vent. In another embodiment where the porous plug is washer shaped having a circumference which is greater than its length, the flow having the longest path can be in the radial direction. The porous vent with the blocking member reduces or eliminates the amount of uncontrolled flow of fluid through the porous vent along the shortest path or the path of least resistance. The sole communication path between the housing interior and the external environment is via the patient puncture tip. The porous vent has a first end face, a second end face, and a central portion extending between the first end face and the second end face. According to one embodiment, the porous vent is configured to cause the fluid to flow along a controlled longitudinal path from the first end face to either the central portion or the second end face of the porous vent and subsequently through a central opening between the first and the second chamber. This central opening can be located adjacent to the central portion of the porous vent. According to another embodiment, the porous vent can be configured to cause the fluid to flow along a controlled longitudinal path from the first end face to the second end face and subsequently into the second chamber through either the first end face and/or the second end face. According to yet another embodiment, the porous vent can be washer shaped having the first end face and the second end face blocked to cause the fluid to flow along a controlled radial path from an inner portion of the porous vent to the outer circumferential end face of the porous vent and into the second chamber.

The blocking member is configured to block at least a portion of the porous vent to render this portion of the vent non-porous to control the flow of fluid therethrough. The blocking member can block at least a portion of an inside surface of the axial hole surrounding at least a portion of the cannula. According to one embodiment, the blocking member comprises a non-porous bushing press-fitted into the inside surface of the porous vent. This bushing can comprise steel or any other type of metal cannula, an extruded plastic tube, a tubular molded part, and the like. The bushing can have a length that is substantially equal to a length of the porous vent. According to another embodiment, the blocking member can comprise an adhesive or sealant located in a space between an inside surface of the porous vent and an outer diameter of the cannula. According to another embodiment, the back end surface of the porous member can be blocked with an adhesive material to control the flow of fluid through the porous vent. According to yet another embodiment, the blocking member can be formed by melting or fusing the inner diameter surface portion of the porous vent. According to another embodiment, the blocking member can be a separate member, such as a plastic tubular or cylindrical member that is placed in abutting relationship with respect to the inside surface of the porous vent. This cylindrical member can extend from a portion of the housing.

According to one design, the at least one cannula can comprise a single cannula extending through the housing. The single cannula can include a lumen extending therethrough, a first end comprising the patient puncture tip, a second end comprising the non-patient puncture tip, and an opening through the cannula into the lumen at a location between the first end and the second end providing fluid communication between the lumen of the cannula and the first chamber of the housing. According to another embodiment, the at least one cannula can comprise a first cannula extending from the housing and comprising the patient puncture tip, and a second cannula extending from the housing and comprising the non-patient puncture tip. The first cannula and the second cannula are substantially axially aligned within the housing interior and separated from each other by a gap in fluid communication with the first chamber of the housing. The first chamber and the second chamber are configured such that upon insertion of the patient puncture tip into a patient causes blood to flow into the first chamber without sealing the porous vent, and upon application of a negative pressure source to the non-patient puncture tip, blood and air are drawn from the first chamber and air is drawn from the second chamber, thereby establishing a negative pressure within the second chamber with respect to an external environment of the needle assembly. Upon removal of the patient puncture tip from the patient, the negative pressure within the second chamber draws blood from the patient needle tip toward the second chamber to prevent blood droplets from being present at the patient puncture tip.

In yet another embodiment, the invention relates to a needle assembly comprising a housing defining a housing interior. The housing comprises at least one cannula having a patient puncture tip extending from a first end of the housing and a non-patient puncture tip extending from a second end of the housing. The non-patient puncture tip and the patient puncture tip are in fluid communication with each other within the housing interior. A porous vent is positioned within the housing interior to separate the housing interior into a first chamber and a second chamber. The porous vent includes pores for passage of fluid therethrough from the first chamber to the second chamber. The porous vent is configured to control flow of the fluid such that the fluid flows along the longest path therethrough. The needle assembly is designed such that the sole communication path between the housing interior and the external environment is via the patient puncture tip and, the first end of the housing comprises an elongate longitudinal first portion having a first diameter and the second end of the housing comprises a second portion having a second diameter larger than the first diameter of the first portion. The porous vent is positioned within the housing interior between the first portion having a first diameter and the second portion having a second diameter at a location spanning a transition point between the first diameter of the first portion and the second diameter of the second portion. The porous vent can comprise a tubular member having a first end face, a second end face, and a central portion located between the first end face and the second end face. The tubular member further includes an axial hole configured for surrounding at least a portion of the cannula. The axial hole defines an inside surface of the porous vent and the assembly further includes a blocking member at the inside surface of the axial hole for blocking at least a portion of the porous vent to render this portion of the vent non-porous to cause the fluid to flow along a controlled longitudinal path from the first end face to either the central location or the second end face and subsequently through a central aperture opening between the first chamber and the second chamber. The blocking member can be a non-porous bushing press-fitted into the inside surface of the porous vent or an adhesive located between an inside surface of the porous vent and an outer diameter of the cannula. Alternatively, the inside portion of the porous vent can be rendered non-porous by fusing this inner surface portion of the porous vent. According to another embodiment, the blocking member can be a separate member, such as a plastic tubular or cylindrical member that is placed in abutting relationship with respect to the inside surface of the porous vent. This cylindrical member can extend from a portion of the housing.

In another embodiment, the invention relates to a needle assembly comprising a housing defining a housing interior. The housing comprises at least one cannula having a patient puncture tip extending from a first end of the housing and a non-patient puncture tip extending from a second end of the housing. The non-patient puncture tip and the patient puncture tip are in fluid communication with each other within the housing interior. A porous vent is positioned within the housing interior separating the housing interior into a first chamber and a second chamber. The porous vent includes pores for passage of fluid therethrough from the first chamber to the second chamber. The porous vent is configured to control flow of the fluid such that the fluid flows in an axial direction therethrough. The housing includes a rear hub which can block a back end face of the porous vent. Alternatively, the rear hub can leave a portion of the second end face exposed. The rear hub includes a cylindrical portion extending therefrom. This cylindrical portion extends into the first chamber toward the first end of the housing to define a portion of the first chamber. The needle assembly is designed such that the sole communication path between the housing interior and the external environment is via the patient puncture tip. The porous vent comprises a tubular member having a first end face, a second end face, and a central portion extending between the first end face and the second end face. The tubular member further includes an axial hole configured for surrounding at least a portion of the cylindrical portion extending from the rear hub. The at least one cannula is located within at least a portion of the cylindrical portion. The cylindrical portion extending from the rear hub into the axial hole of the porous vent abuts against the inside surface of the porous vent to act as a blocking member to render a portion of the vent non-porous and to cause the fluid to flow along a controlled longitudinal path and consequently through either a central aperture opening between the first and the second chamber or through either the first end face or the second end face of the porous vent. An adhesive can be located between an inside surface of the porous vent and an outer diameter of the cannula and/or the cylindrical portion or the inner surface portion of the porous vent can be fused to render this portion non-porous in order to assist in controlling the flow of fluid through the porous vent.

According to still another embodiment, the invention relates to a method of preventing leakage of a blood droplet from a patient puncture tip of a needle assembly. The method includes: a) receiving blood through a patient puncture tip and into a first chamber of a needle assembly, the needle assembly comprising: i) a needle housing defining a housing interior, the housing comprising at least one cannula having a patient puncture tip extending from a first end of the housing and a non-patient puncture tip extending from a second end of the housing; and ii) a porous vent positioned within the housing interior and separating the housing interior into a first chamber and a second chamber, with the non-patient puncture tip and the patient puncture tip being in fluid communication with each other within the first chamber such that the sole communication path between the housing interior and the external environment is via the patient puncture tip. The porous vent includes pores for passage of blood and air therethrough from the first chamber into the second chamber and the porous vent is configured to control flow of the blood and air such that the blood and air flows along the longest path therethrough. The method further includes: b) establishing fluid communication between the non-patient puncture tip and a negative pressure source such that blood contained within the first chamber is drawn out of the non-patient puncture tip and air is drawn out of the second chamber through the porous vent, thereby establishing a negative pressure within the second chamber relative to the external environment of the needle assembly such that blood flows through the cannula into the first chamber and contacts the porous vent; and c) drawing blood and air through the pores of the porous vent toward the second chamber based upon the negative pressure established within the second chamber such that blood contained within a lumen of the patient puncture tip is displaced away from the patient puncture tip and toward the second chamber. The method is such that the receiving step a) comprises receiving blood through the lumen of the patient puncture tip from a patient's bloodstream, and the drawing step c) displaces blood away from the patient puncture tip after removing the patient puncture tip from the source of blood, such as, for example, from the vein. The method further includes the step that after step b) and prior to step c), releasing the fluid communication between the non-patient puncture tip and the negative pressure source. The porous vent can comprise a tubular member having a first end face and a second end face and wherein the tubular member further includes an axial hole configured for surrounding at least a portion of the cannula. The method includes rendering the inside surface of the axial hole non-porous to cause the fluid to flow along the longest path through the porous vent and subsequently into the second chamber. Depending upon the shape of the porous vent, this longest path can be a longitudinal path or a radial path. A blocking member can be provided to render the inside surface of the axial hole non-porous. This blocking member can be a bushing formed from a non-porous metal or plastic material press-fitted into the inside surface of the porous vent, an adhesive located between an inside surface of the porous vent and an outer diameter of the cannula, a fused inner surface portion of the porous vent, and/or a separate member that is placed in an abutting relationship with respect to the inside surface of the porous vent.

DESCRIPTION OF THE DRAWINGS

FIG. 11A is a cross-sectional view of the needle assembly having a flash chamber of FIG. 8.
FIG. 11B is an enlarged cross-sectional view of a portion of the needle assembly of FIG. 11A.
FIG. 12A is a cross-sectional view of a needle assembly having a flash chamber used in connection with a blood collection assembly in yet a further embodiment.
FIG. 14 is a perspective view of the needle assembly of FIG. 13A shown in combination with a blood collection holder, with a needle shield in a shielding position.
FIG. 22A shows a cross-sectional view of the needle assembly according to an alternative design of the invention.
FIG. 22B shows a cross-sectional view of the needle assembly according to another design of the invention.
FIG. 23A shows a cross-sectional perspective view of the needle assembly of the invention according to another design.

DETAILED DESCRIPTION

Figure 1:
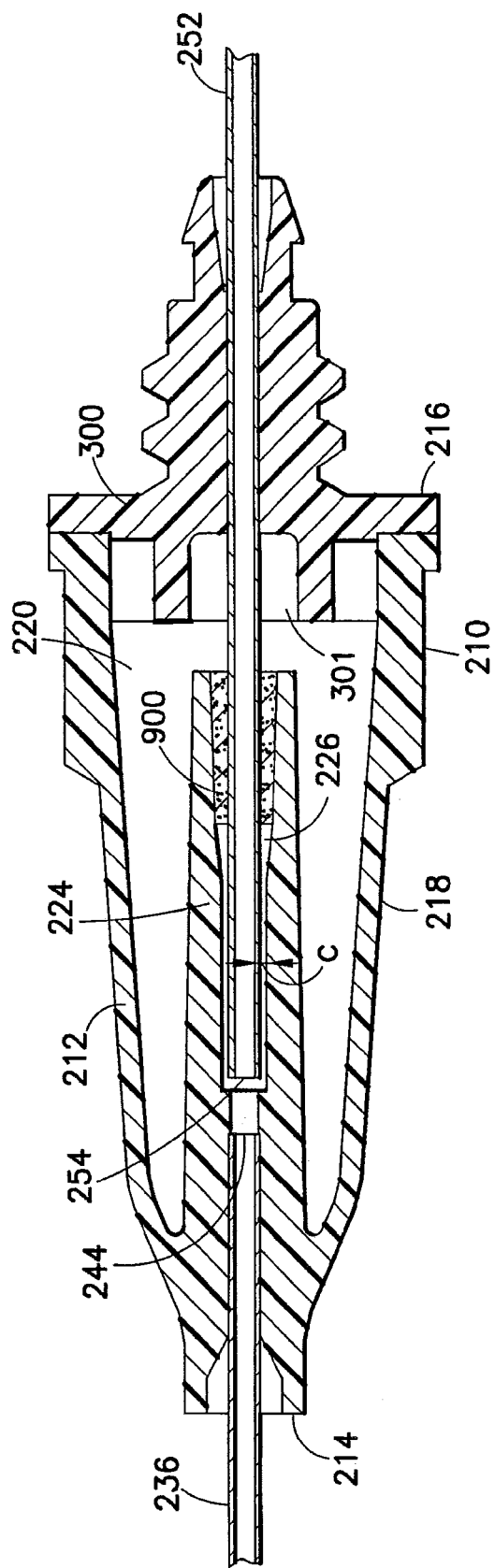
FIG. 1 is a cross-sectional view of a typical embodiment of the needle assembly of the present invention.

An embodiment of the invention provides a needle assembly for blood collection that provides a visual indication of vein entry ("flashback") upon collection of a blood or other fluid sample from a patient into one or more evacuated blood collection tubes and inhibits leakage of the blood or fluid sample from the IV cannula on removal from the patient.

Various embodiments of the present invention are shown in the FIGS. With reference to FIGS. 1-6, this embodiment is directed to a needle assembly 210 with a housing 212 having a fluid inlet end 214, a fluid outlet end 216 and a frustum-shaped exterior wall 218 extending between the ends. Exterior wall 218 defines the housing interior 220. Housing 212 further includes a cylindrical interior wall 224 that extends in the housing interior 220 from fluid inlet end 214 substantially concentrically with cylindrical exterior wall 218 to a vent plug 900. Cylindrical interior wall 224 and vent plug 900 define a flashback chamber 226.

Needle assembly 210 also includes a fluid inlet cannula 236 having an exterior end that defines a sharpened bevel and an interior end 244 that is mounted fixedly in fluid inlet end 214 of housing 212. Fluid inlet cannula 236 is characterized further by a substantially cylindrical lumen extending between the ends and communicating with the interior of housing 212.

Figure 5:
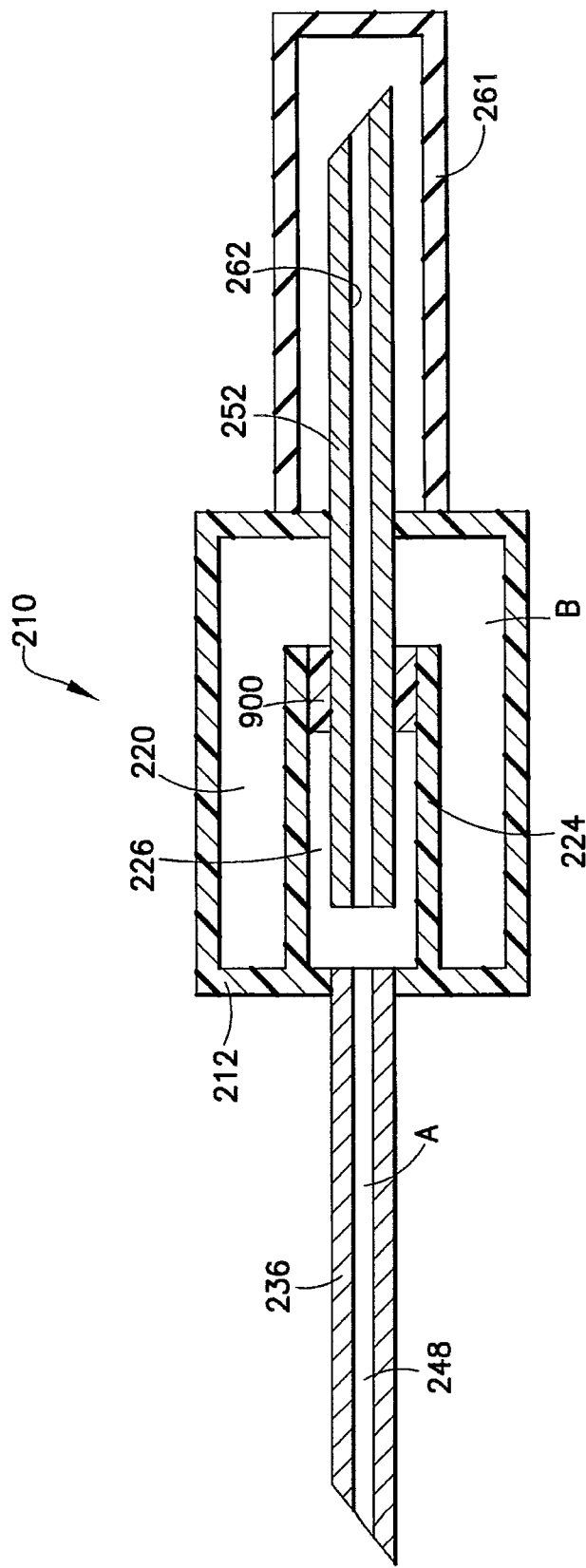
FIG. 5 is a schematic view of the needle assembly of FIG. 1 prior to use.
Figure 6:
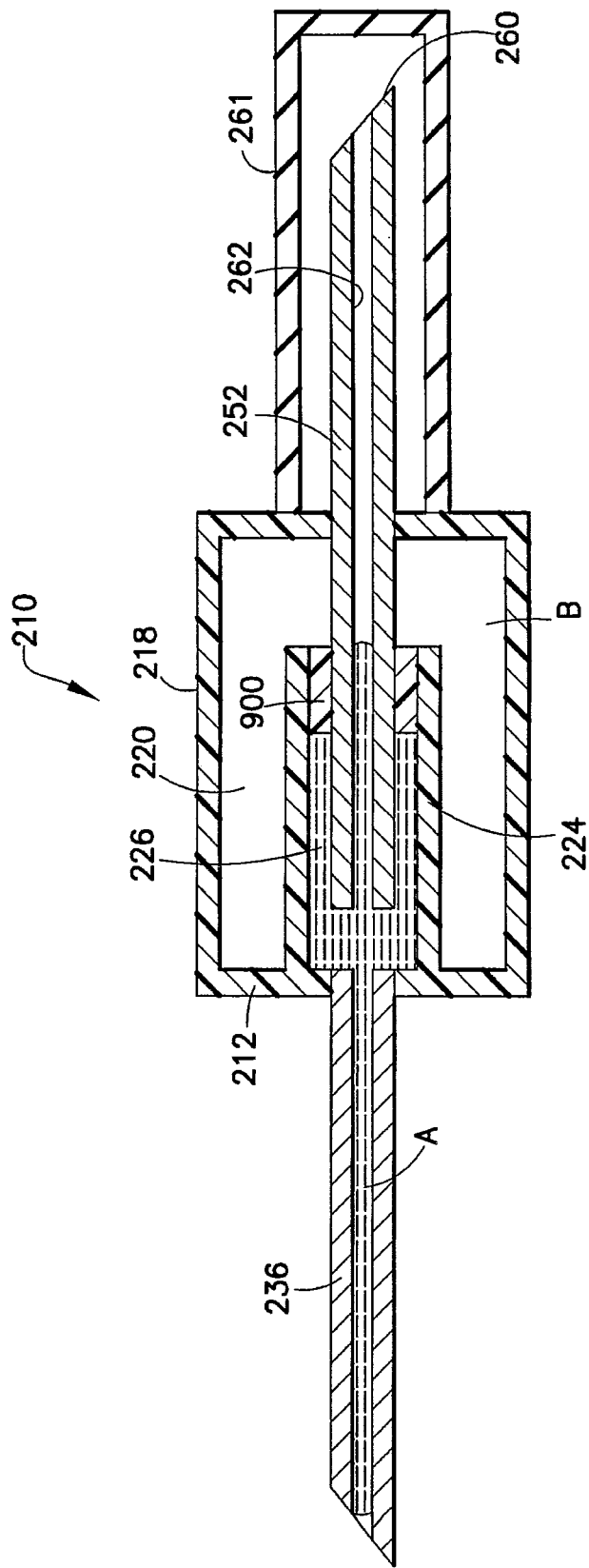
FIG. 6 is a schematic view similar to FIG. 5, but showing the first sign of venous entry.

Needle assembly 210 further includes a fluid outlet cannula 252. With reference to FIGS. 5-6, outlet cannula 252 concludes a blunt interior end 254, an exterior end defining a sharpened bevel and a substantially cylindrical lumen extending between the ends. Portions of outlet cannula 252 between the ends are securely affixed in outlet end 216 of housing 212. Outlet cannula 252 is mounted so that interior end 254 passes substantially coaxially into interior wall 224 and so that interior end 254 of outlet cannula 252 substantially aligns axially with interior end 244 of inlet cannula 236. Additionally, interior end 254 of outlet cannula 252 is spaced only a small distance from interior end 244 of inlet cannula 236. An axial gap between interior end 254 of outlet cannula 252 and interior end 244 of inlet cannula 236 that is less than 0.5 mm may result in a flashback that is inconsistent.

Cylindrical interior wall 224 is dimensioned relative to outlet cannula 252 to achieve both desirable flow of blood through assembly 210 and to achieve effective flashback indication. In particular, cylindrical interior wall 224 preferably is dimensioned to provide a radial gap around outlet cannula 252 of about 0.2 mm, as indicated by dimension "c" in FIG. 1. This gap achieves a substantially laminar blood flow within flashback chamber 226 and prevents blood hemolysis. Additionally, the small radial gap between cylindrical inner wall 224 and outlet cannula 252 enables a drop of blood to be spread thinly across the radial gap in flashback chamber 226 to provide a magnified flashback indication with a very small volume of blood. Thus, an easily visualized flashback indication is achieved quickly at the first appearance of blood from interior end 244 of inlet cannula 236.

Needle assembly 210 further includes a sealable sleeve 261 mounted to fluid outlet end 216 of housing 212 and covering exterior end 258 of outlet cannula 252 when sealable sleeve 261 is in an unbiased condition. However, sealable sleeve 261 can be collapsed in response to pressure exerted by the stopper of an evacuated tube for urging exterior end 260 of outlet cannula 252 through both sealable sleeve 261 and stopper of an evacuated tube, as known in the art.

The above embodiment is described in terms of a vent plug. However, any vent mechanism is suitable. The vent mechanism may be, for example, a porous vent plug formed from a matrix or carrier material, typically hydrophobic, that is coated with, impregnated with, or otherwise, contains a hydrophilic material that swells on contact with aqueous or water containing substances. The hydrophobic carrier material can be but is not limited too, high-density polyethylene, polytetrafluoroethylene, ultra-high molecular weight polyethylene, Nylon 6, polypropylene, polyvinylidine fluoride and polyethersulfone. The swellable nature of the hydrophilic material thereby provides the sealing function in the vent upon contact with blood. It is also possible to use a porous vent plug that becomes sealed upon contact with blood using biological phenomena, e.g., by clotting and/or cell agglutination that blocks the vent; a superabsorbant material to seal the vent by swelling on contact with an aqueous fluid; a porous vent configured to form a tortuous path for fluid movement therethrough; or a one-way valve, (e.g., a thin flap such as plastic film covering a vent, a deformable seal such as a rubber or plastic duckbill valve, or a deformable wrap over a vent). It should be noted that any combination of these various mechanisms is also possible.

Figure 2:
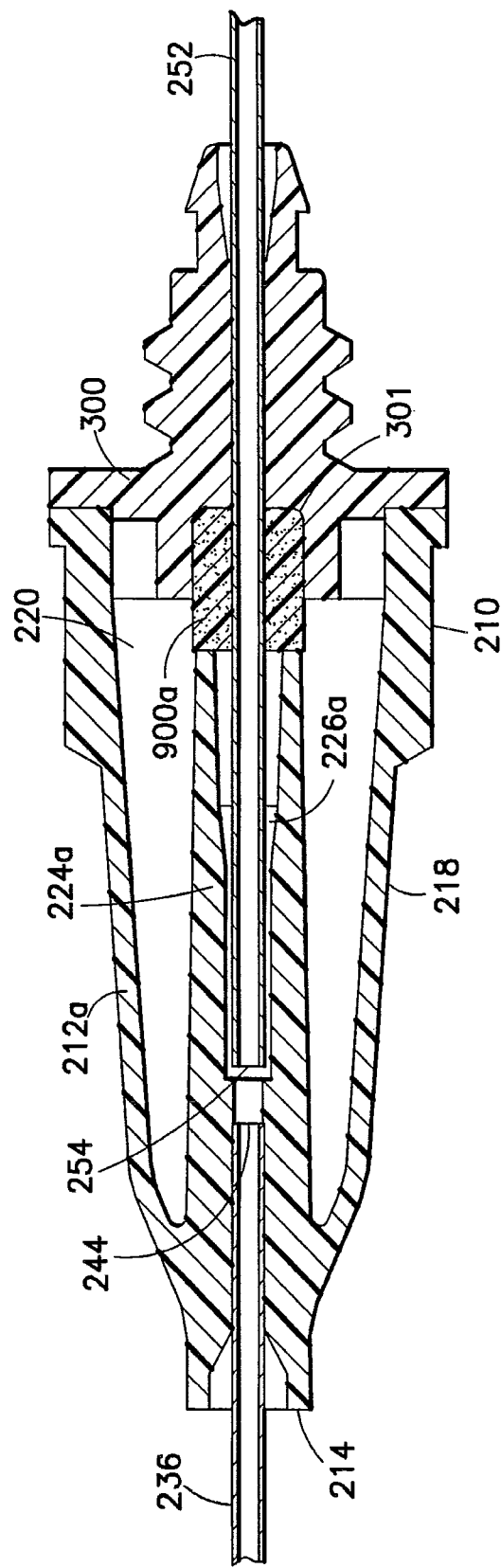
FIG. 2 is a cross-sectional view of a second embodiment.
Figure 3:
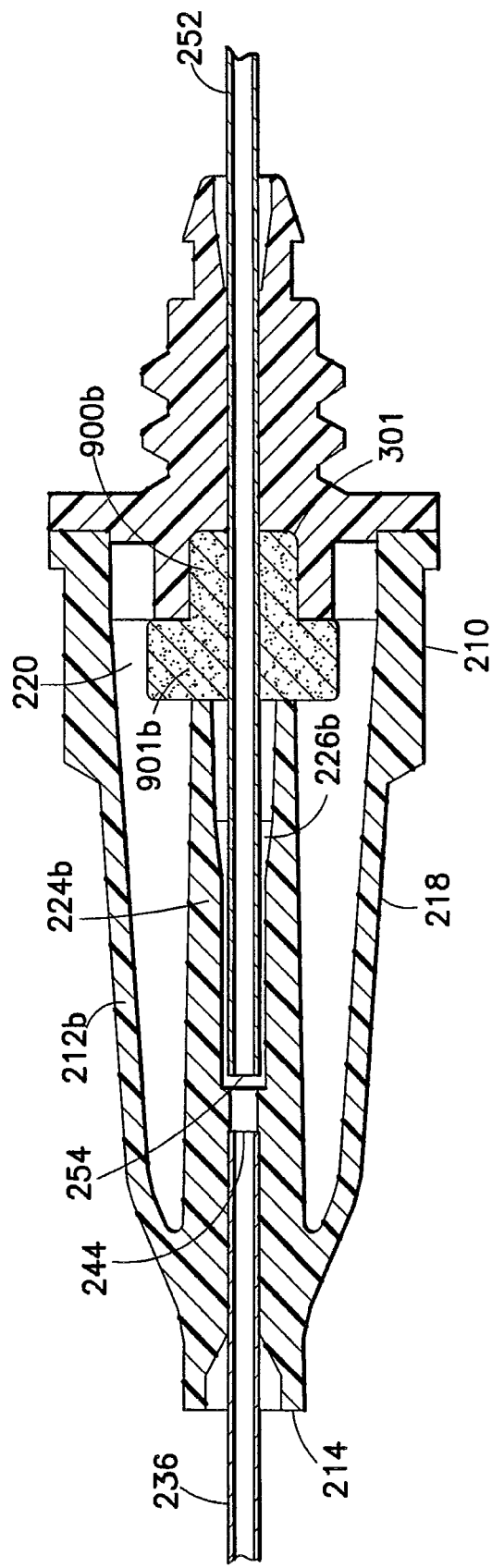
FIG. 3 is a cross-sectional view of a third embodiment.
Figure 4:
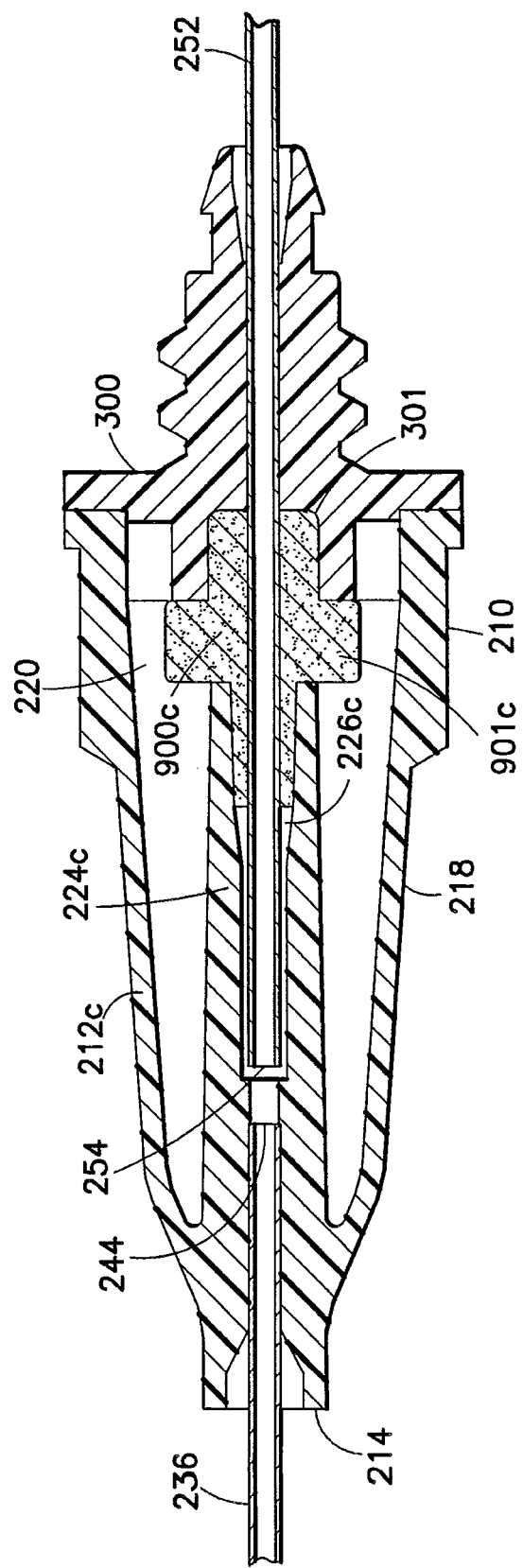
FIG. 4 is a cross-sectional view of a fourth embodiment.

FIGS. 2-4 show embodiments with varying vent plugs. FIG. 2 shows a vent plug 900a, which is located at the end of the cylindrical inner wall 224a and fitted into a recess 301 in the housing interior non-patient wall 300. FIG. 3 shows a vent plug in a similar location to that of FIG. 2, however, vent plug 900b has a shoulder 901b. FIG. 4 shows a vent plug 900c that is located both within the cylindrical inner wall 224c and the recess 301 in the housing interior non-patient wall 300, and has a shoulder 901c. The vent plug location in each of these embodiments is such that no air can flow out of the flashback chamber 226 into the housing interior 220 without passing through the vent mechanism (900 a, b, c).

FIGS. 5 and 6 provide schematic representations of the needle assembly 210 of FIG. 1 before and after a conventional venipuncture, in which, the needle assembly 210 is connected to a holder (not shown) and punctures the patient's skin to make a vein entry. Upon vein entry, blood enters the IV cannula 236 and flows toward the flashback chamber 226. The blood flows from inlet cannula 236 into the space between inlet and outlet cannula, such that blood flows both into the outlet cannula 252 and into flashback chamber 226. At this point in time, flashback chamber 226, indicates successful vein entry and reduces the volume of air present in housing 212 shown in FIG. 6. Air that was at atmospheric pressure within the lumen of the IV cannula 248, flashback chamber 226, housing interior 220, and the lumen of the non-patient cannula 262 prior to vein entry, thus experiences compression due to the influence of venous pressure and this air is therefore forced through the IV cannula 236 shown in FIG. 6 into the flashback chamber 226 and through the vent plug 900 into chamber 220. Blood flow into housing interior 220 is prevented by the vent plug 900, which allows the pressurized air to flow through it, but seals, and sometimes completely seals, on contact with blood, thereby trapping the compressed air (at venous pressure) in housing interior 220. Blood flow in the entire needle assembly ceases once the pressure within chamber 226 and the venous pressure are equal.

Once the steps set forth in the previous paragraph occur, and venous entry is visually confirmed by the phlebotomist, an evacuated container (not shown), is then inserted into the holder such that exterior end 260 of second cannula 252 penetrates the stopper of the container, as known in the art. Upon penetration of the stopper by second cannula 252, a negative pressure gradient is transmitted to chamber 226, causing blood to flow from chamber 226 into the container.

The needle assemblies described above desirably should be small for convenient use, but should be constructed to ensure reliable and rapid flashback. The occurrence of flashback in the needle assemblies described and illustrated above operate pursuant to the ideal gas law. In particular, at very low densities all gases and vapors approach ideal gas behavior and closely follow the Boyle's and Charles' laws given by:

$$P_1V_1 = P_2V_2$$

where:
- $P_1$ denotes the pressure of air within the needle assembly before needle insertion;
- $P_2$ denotes the pressure of air within the needle assembly after vein entry;
- $V_1$ denotes the volume of air within the needle assembly before vein entry; and
- $V_2$ denotes the volume of air within the needle assembly after vein entry.

Design parameters should keep the needle device as small as possible for easy use, while ensuring an appropriate volume as specified by the preceding equation. FIGS. 5 and 6 provide schematic representations of the needle assembly 210 of FIG. 1 for purposes of depicting the application of the ideal gas law. In this regard, A identifies the volume of lumen 248 through inlet cannula 236. B denotes the total volume of the housing interior 220, flashback chamber 226, lumen 242 through outlet cannula 252 and sealable sleeve 261. Referring again to the preceding equation, $P_1$ is the pressure within needle assembly 210 before use, and hence substantially equals atmospheric pressure. Atmospheric pressure will vary slightly from time to time and from location to location. However, for purposes of this analysis, atmospheric pressure $P_1$ will be assumed to be 760 mm Hg. $P_2$ in the preceding equation is the volume of the dead space in needle assembly 210 after vein entry. More particularly, after vein entry, blood will fill lumen 248 of inlet cannula 236, thereby reducing the volume to be occupied by gas in remaining portions of needle assembly 210 and hence increasing the pressure of air in the remaining portion of needle assembly 210. A needle assembly with dimensions approximately as shown in FIG. 1 will have a pressure $P_2$ of about 790 mm Hg at venous pressure (with tourniquet). $V_1$ in the preceding equation defines the volume of the total dead spaced in needle assembly 210 before use, and hence will equal A+B as shown in FIG. 5. $V_2$ defines the dead space in the device after vein entry, and with lumen 248 of inlet cannula 236 filled with blood. Hence, $V_2$ in the preceding equation will equal B. These input parameters can be employed to define a minimum desired size for the respective components of needle assembly 200 as shown in the following application of the ideal gas law equation.

$$P_1V_1 = P_2V_2$$

$$P_1/P_2 = V_2/V_1$$

$$760/790 = B/(A+B)$$

$$0.962 = B/(A+B)$$

$$0.962(A+B) = B$$

$$0.038B = 0.962A$$

$$B = 25.3A$$

Therefore, dead space in housing 212, outlet cannula 252 and sleeve 261 advantageously is at least 25.3 times the volume defined by lumen 248 through inlet cannula 236 and most advantageously is about 26 times the volume of lumen 248. However, other configurations are possible and will function as described herein.

The immediate response when an evacuated tube is placed in communication with outlet cannula 252 is to draw blood from the vein into tube (not shown). The highest-pressure gradient is always maintained between the vein and the evacuated tube. An axially aligned inlet cannula 236 and outlet cannula 252, therefore provide an unobstructed path for blood flow from the vein into evacuated tube.

When the requisite tubes are filled with blood, the needle assembly is removed from the vein. The sealed nature of the vent plug 900 inhibits the pressurized air within housing interior 220 from then moving into the flashback chamber 226 and into the inlet cannula 236, which could promote dripping of blood from the IV cannula tip.

Figure 7:
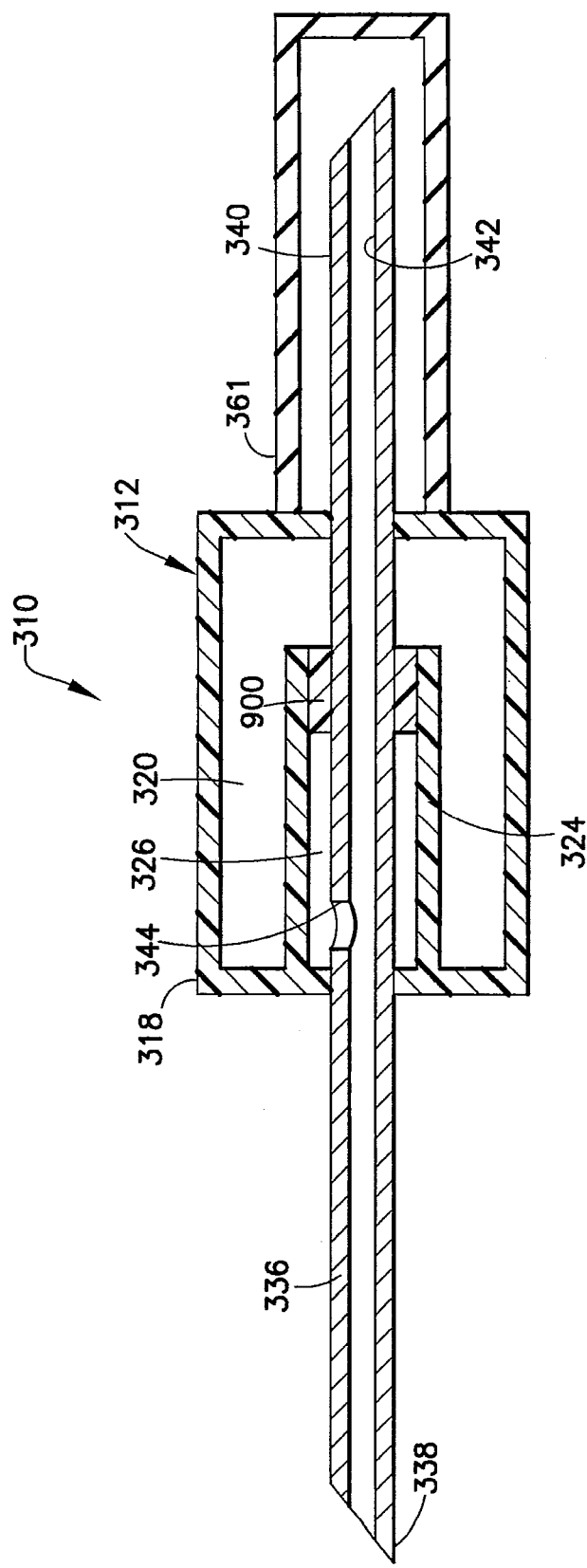
FIG. 7 is a schematic view of a fifth embodiment.
Figure 8:
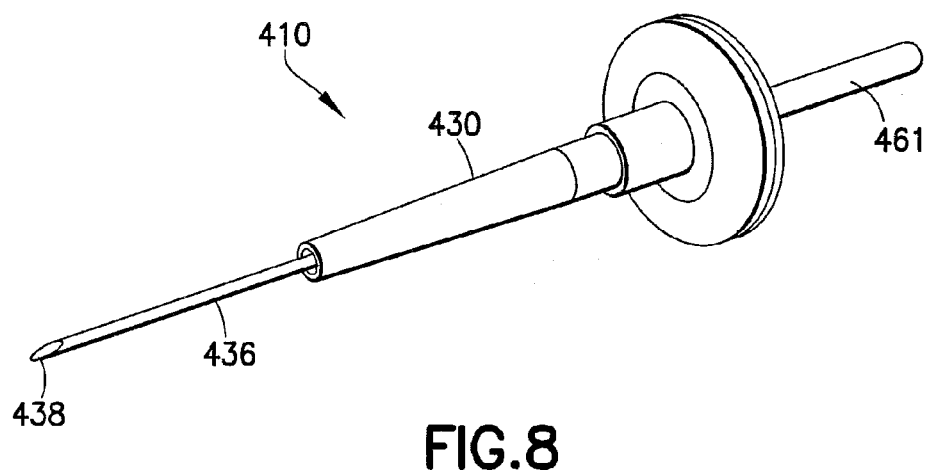
FIG. 8 is a perspective view of a needle assembly having a flash chamber in a further embodiment.
Figure 9:
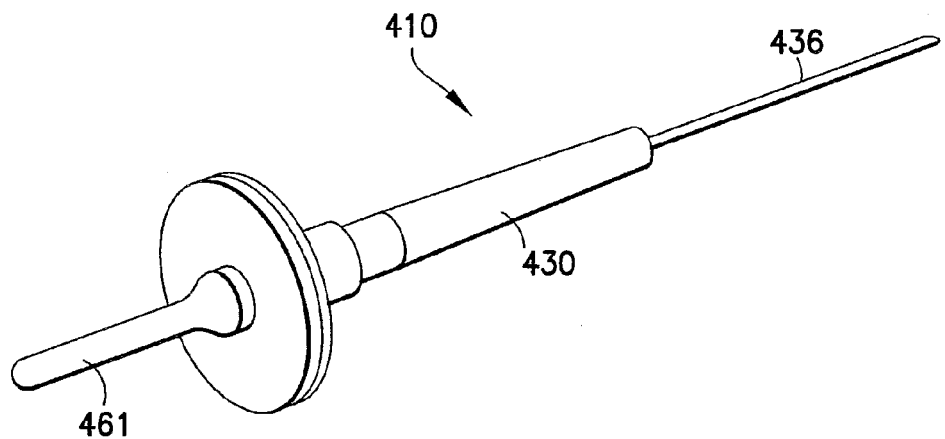
FIG. 9 is a rear perspective view of the needle assembly having a flash chamber of FIG. 8.

The preceding embodiments show structurally separate inlet and outlet cannulas that are axially aligned with one other and placed in close end-to-end relationship with one another. However, the principals of the invention described above also can be achieved with a single cannula formed with a transverse slot or aperture within the flashback chamber. For example, FIG. 7 schematically shows a needle assembly 310 with a housing 312 and housing interior 320 that is substantially identical to housing 212 described and illustrated above. Needle assembly 310 differs from needle assembly 210 in that a single double end needle cannula 336 is provided and passes entirely through housing 312. More particularly, needle cannula 336 includes a venous entry end 338, a non-patient end 340 and a lumen 342 extending therebetween. Portions of cannula 336 within inner wall 324 include a slot or aperture 344 to provide communication between lumen 342 and flashback chamber 326 within inner wall 324. Needle assembly 310 functions substantially in the same manner as needle assembly 210 described and illustrated above.

FIGS. 8-10, 11A, and 11B depict a needle assembly in yet a further embodiment of the invention. In certain embodiments of the needle assembly described with respect to FIGS. 1-7, the housing interior includes a vent plug 900, which seals the flashback chamber 226/326 from the housing interior 220/320. In such previously described embodiments, the vent plug is described as sealing upon flow of blood into the flashback chamber, thereby inhibiting any pressurized air that may build up within the housing chamber 220/320 (such as upon displacement of air from the flashback chamber 226/326 into the housing chamber 220/320 during the initial flash procedure) from moving in a reverse direction toward the inlet cannula. In the embodiment of FIGS. 8-10, 11A and 11B, a porous vent is positioned within the housing at a location such that the vent divides the housing into two chambers having sizes and dimensions to establish predetermined volumes thereto. Moreover, the porous vent remains porous to blood and does not seal upon contact with blood. Desirably the blood does not contact the porous vent at the initial flash indication, but such contact occurs at a later point during use of the assembly, as will be described in more detail herein.

For example, FIGS. 8-10, 11A, and 11B show a needle assembly 410 similar to that described in connection with FIG. 1-6 above. As shown in FIGS. 8-10, 11A, and 11B, needle assembly 410 includes a housing 412 having a fluid inlet end or first end 414 and a fluid outlet end or second end 416. Needle assembly 410 includes exterior wall 418 defining the housing interior. Exterior wall 418 extends generally longitudinally at the first end 414 forming an elongate longitudinal first portion 419 having a first diameter. At second end 416, exterior wall 418 forms a second portion 421 that has a second diameter that is generally larger than the first diameter of the first portion 419. Accordingly, housing 412 may form a structure having a generally T-shaped cross-section. The exterior wall 418 at second end 416 may be a separate element 428 that is attachable to main body portion 430 forming housing 412, thereby assisting in manufacture and assembly of needle assembly 410. First portion 419 and second portion 421 may be arranged relative to each other in a variety of arrangements, so long as they are capable of functioning for transport of air therebetween as discussed herein.

Needle assembly 410 further includes a fluid inlet cannula 436 extending from first end 414 of housing 412. Fluid inlet cannula 436 includes an exterior end that defines a first puncture tip such as a sharpened bevel at patient puncture tip 438, and extends within first end 414 of housing 412 at open end 429, and may be fixedly mounted therein. Fluid inlet cannula 436 is characterized further by a substantially cylindrical lumen extending between the ends and communicating with the interior of housing 412.

Figure 10:
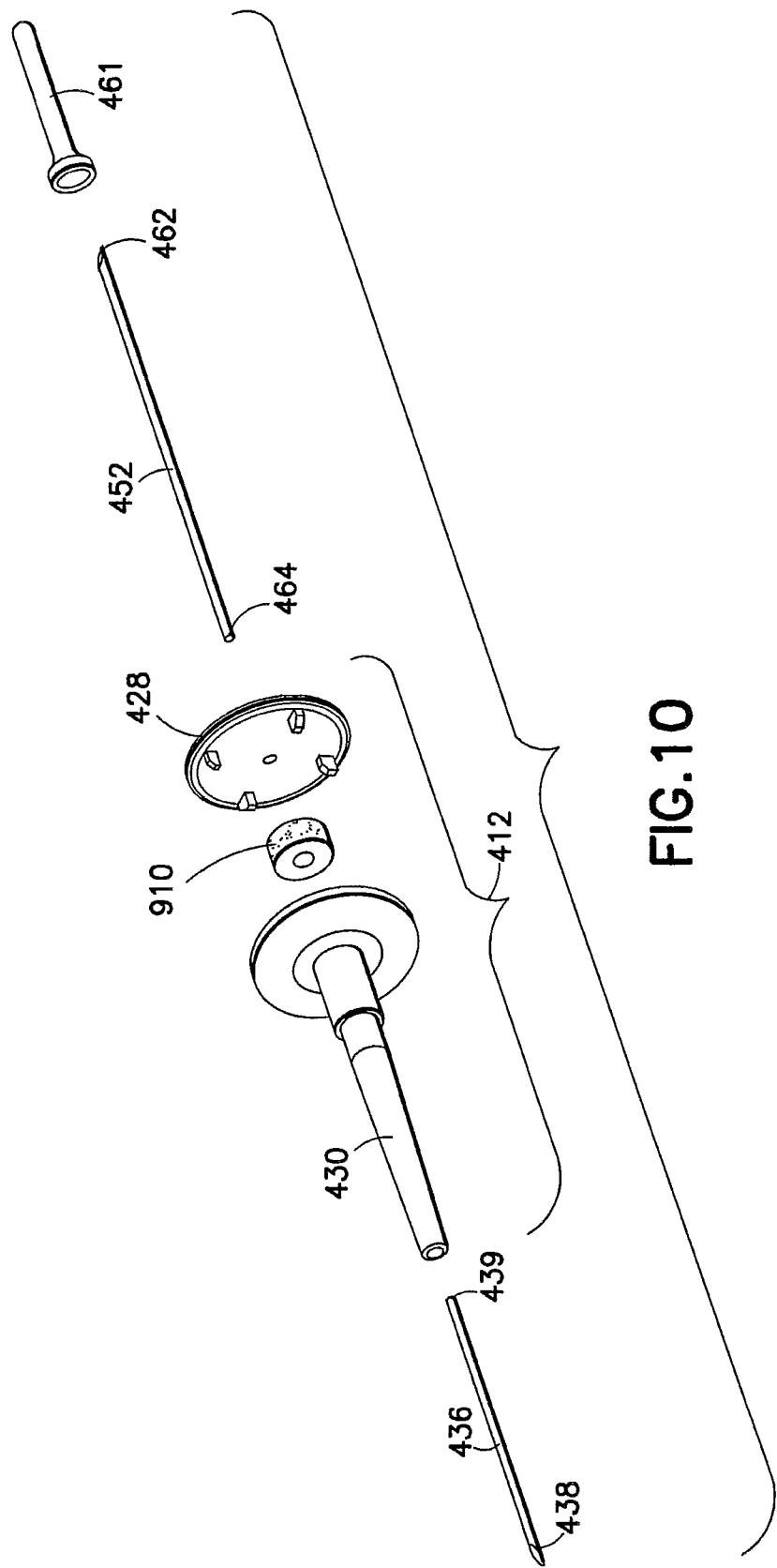
FIG. 10 is an exploded view of the needle assembly having a flash chamber of FIG. 8.

Needle assembly 410 also includes a second puncture tip such as non-patient puncture tip 462 extending from second end 416 of housing 412. As seen in FIG. 10, this may be accomplished by providing needle assembly 410 with a second cannula in the form of fluid outlet cannula 452. In particular, the end of fluid outlet cannula 452 may define a sharpened bevel forming non-patient puncture tip 462. Fluid outlet cannula 452 extends within second end 416 of housing 412, and may be fixedly mounted therein. Fluid outlet cannula 452 is characterized further by a substantially cylindrical lumen communicating with the interior of housing 412. Outlet cannula 452 is mounted within housing 412 so that an interior end 464 passes substantially coaxially therein such that outlet cannula 452 substantially aligns axially with the interior end of inlet cannula 436. Desirably, this is achieved by mounting outlet cannula 452 at a location adjacent second end 416 of housing 412, such that the interior end 464 of outlet cannula 452 extends within housing 412 to a location adjacent the interior end 439 of inlet cannula 436. As seen in FIG. 11B, the interior end 464 of outlet cannula 452 is spaced only a small distance from the interior end 439 of inlet cannula 436, thereby forming an axial gap therebetween for flow of blood into flashback chamber 426 about outlet cannula 452. The distance between the interior end 464 of outlet cannula 452 and the interior end 439 of inlet cannula 436 forming the axial gap is sufficient to provide for flow of blood into flashback chamber 426, based upon the patient's blood pressure after venipuncture. In certain embodiments, an axial gap that is less than 0.5 mm may result in a flashback that is inconsistent.

As seen in FIG. 11B, fluid inlet cannula 436 and fluid outlet cannula 452 are positioned and dimensioned within housing 412 so as to achieve both desirable flow of blood through assembly 410 and to achieve effective flashback indication. In particular, wall 418 of housing 412 is dimensioned to provide a radial gap around outlet cannula 452 of about 0.2 mm at an area surrounding the internal end 464 thereof. This gap achieves a substantially laminar blood flow within flashback chamber 426 and prevents blood hemolysis. Additionally, the small radial gap between the inner surface of wall 418 and outlet cannula 452 at the area surrounding the internal end 464 enables a drop of blood to be spread thinly across the radial gap in flashback chamber 426 to provide a magnified flashback indication with a very small volume of blood. Thus, an easily visualized flashback indication is achieved quickly at the first appearance of blood within flashback chamber 426. It is contemplated that internal end 464 of outlet cannula 452 may be partially supported within housing 412, so long as blood flow into flashback chamber 426 is achieved about the internal end 464.

Figure 12B:
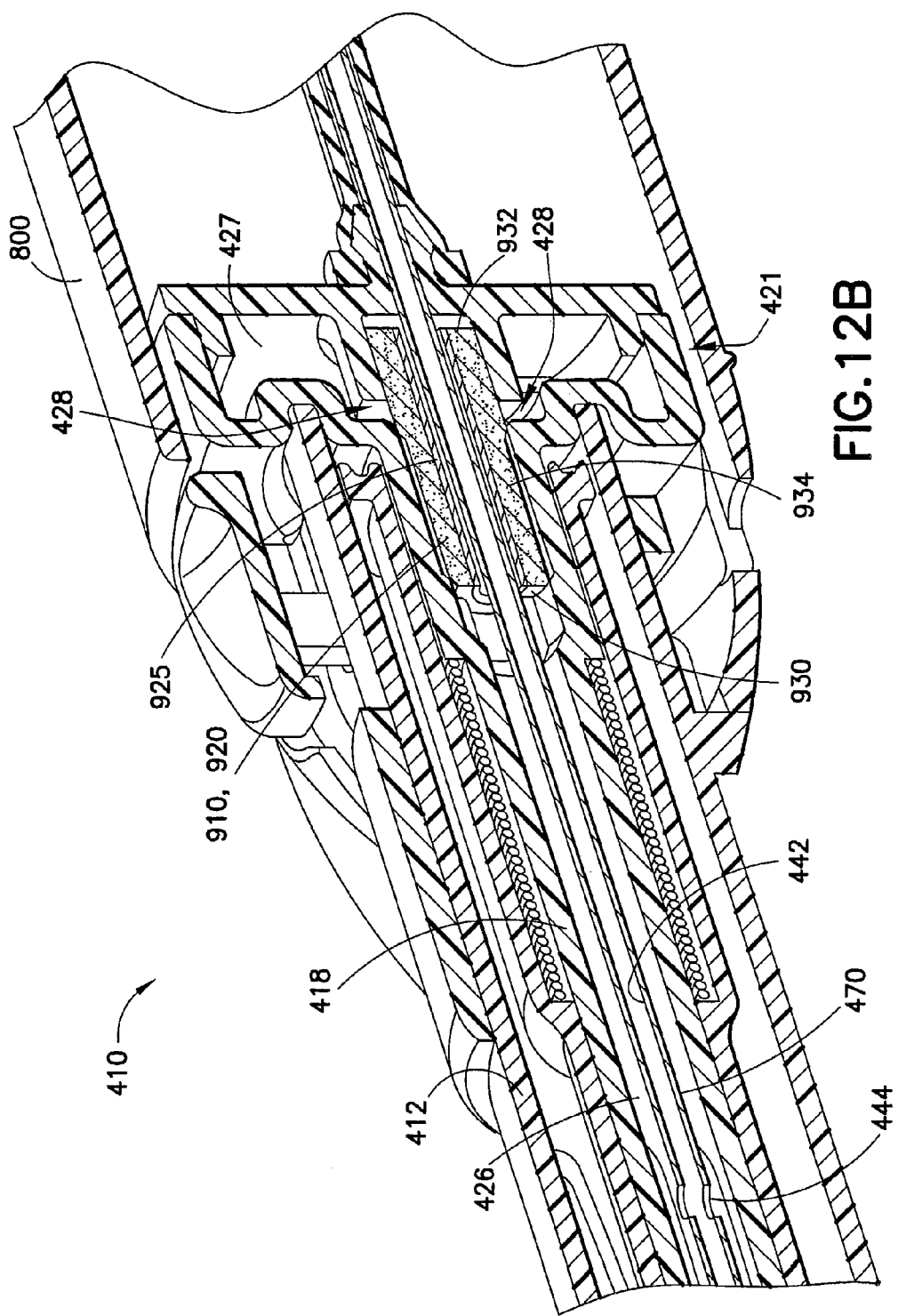
FIG. 12B is an enlarged sectional view of a portion of the needle assembly of FIG. 12A.

In an alternate arrangement, a single cannula is provided, similar to that embodiment discussed in connection with FIG. 7. Such an arrangement is depicted in the embodiment of FIGS. 12A and 12B (shown in connection with a blood collection assembly as will be described in more detail herein). In such an arrangement, the fluid inlet cannula and the fluid outlet cannula represent one single cannula 470, having a patient puncture tip 438 a non-patient puncture tip 462, and a lumen 442 extending therethrough, and with the body of the cannula 470 being fixedly attached to a portion of the housing 412 and passing entirely through housing 412. A portion of cannula 470 extending through housing 412 includes one or more openings such as a slot or aperture 444 to provide communication between lumen 442 and flashback chamber 436 within housing 412. In the embodiment seen in FIGS. 12A and 12B, two semi-circular cuts forming the aperture are shown on opposing sides of cannula 470, although it is contemplated that any number of such openings can be included to provide for blood flow into flashback chamber 426.

Returning to the embodiment of FIGS. 8-10, 11A, and 11B, needle assembly 410 further includes a sealable sleeve 461 mounted to fluid outlet end 416 of housing 412. This may be accomplished by providing a mounting protrusion 429 at second end 416 of housing 412, such as on element 428, with sealable sleeve 461 representing an elastomeric element that can be frictionally fit or otherwise affixed over protrusion 429. Sealable sleeve 461 covers non-patient puncture tip 462 at the exterior end of outlet cannula 452 when sealable sleeve 461 is in an unbiased condition. However, sealable sleeve 461 can be collapsed in response to pressure exerted by the stopper of an evacuated tube for urging exterior end 462 of outlet cannula 452 through both sealable sleeve 461 and the stopper of an evacuated tube, as known in the art.

The embodiment of FIGS. 8-10, 11A, and 11B further includes a porous vent 910 positioned within the interior of housing 412. Porous vent 910 is positioned within housing 412 to divide housing 412 into two distinct chambers, namely, a first chamber represented by flashback chamber 426 and a second chamber represented by secondary chamber 427. Porous vent 910 may be constructed of a suitable material as described above with respect to vent plug 900, albeit without the hydrophilic material that swells on contact. In this manner, porous vent 910 is adapted to vent air therethough, and represents a porous structure including a plurality of pores that allow for passage of blood therethrough without sealing from fluid flow therethrough upon contact with blood, as is known in the art with vent plugs including a hydrophilic material. As discussed in more detail herein, during use of needle assembly 410, the internal pores within porous vent 910 at least partially fill with blood due to the negative pressure established within secondary chamber 427. Such filled pores in combination with the negative pressure within secondary chamber 427 prevent air flow between the secondary chamber 427 and the flashback chamber 426, and provide for fluid resistance of the blood flow through porous vent 910, as will be described in further detail.

Desirably, porous vent 910 is positioned within the interior of housing 412 between first portion 419 and second portion 421. In this manner, first portion 419 of housing 412 essentially defines the flashback chamber 426, and second portion 421 of housing 412 essentially defines the secondary chamber 427. Alternatively, porous vent 910 may be positioned within the interior of housing 412 at a location spanning the transition between the first diameter of first portion 419 and the second diameter of second portion 421, as shown in the embodiment of FIGS. 12A and 12B. In any event, porous vent 910 is generally a cylindrically-shaped member with a central opening therein axially encircling a portion of the cannula, particularly fluid outlet cannula 452.

The interior volume of housing 412 is defined by the sum of the volumes of flashback chamber 426 and secondary chamber 427 as well as the volume represented by the pores of porous vent 910. Such interior volume is configured so as to provide for certain attributes to the needle assembly 410, in particular with respect to the ability of the secondary chamber 427 to be at least partially evacuated of a portion of the air therein to establish a negative pressure therein upon application of an evacuated tube to needle assembly 410 during use thereof. Such negative pressure within secondary chamber 427 draws blood through the pores of porous vent 910 based on when blood contacts porous vent 910 and partially fills the pores thereof. In a particular embodiment of the invention, the overall interior volume of housing 412 may be from about 300 mm$^3$ to about 400 mm$^3$. Such a volume is particularly useful for the intended use of needle assembly 410 for conventional venipuncture for drawing a blood sample from a patient using a needle cannula having a conventional gauge for venipuncture as is known in the art. Such a volume also enables the needle assembly to be particularly useful with patients having relatively low blood pressure, in that the interior volume of the housing 412 is sufficient so as to allow adequate displacement of air so that blood will travel the complete length of fluid inlet cannula 436 and into flashback chamber 426.

Porous vent 910 is desirably positioned within housing interior so as to define flashback chamber 426 as having a volume that represents from about 5 percent to about 20 percent of the total overall volume of housing 412, desirably from about 7 percent to about 12 percent of the total overall volume of housing 412, including the volume of secondary chamber 427 and the volume of the pores within porous vent 910. In this manner, the remaining internal volume of housing 412, defined by the internal volume positioned downstream from the interface between porous vent 910 and flashback chamber 426 including the internal pores of porous vent 910 and the volume of secondary chamber 427, represents a significant portion of the internal volume of housing 412. Such a ratio of the flashback chamber 426 to the total overall volume of the housing 412 assures that flashback chamber 426 has sufficient volume to properly visualize the initial flash, desirably while preventing blood from fully contacting the porous vent 910 at initial venipuncture, based on the initial build-up of pressure within secondary chamber 427 caused by venous pressure forcing the blood into flashback chamber 426. Such volume ratios are effective for the intended use as described in further detail herein, wherein blood flowing into flashback chamber 426 upon initial venipuncture does not fully contact porous vent 910, and desirably does not contact porous vent 910, and wherein at least a portion of the air is drawn out from secondary chamber 427 based upon application of an evacuated blood collection tube to the needle assembly 410. In this manner, secondary chamber 427 can effectively draw blood from within flashback chamber 426 and from within fluid inlet cannula 426 toward secondary chamber 427, such as into and through the pores of porous vent 910, so that when the patient puncture tip 438 is removed from the patient and is exposed to the external environment, blood is drawn away from the puncture tip 438, preventing the leakage of blood droplets from the puncture tip 438. In one particular embodiment, the total interior volume of the housing 412 is about 380 mm$^3$, with the flashback chamber 426 having a volume of about 30 mm$^3$, the secondary chamber 427 having a volume of about 300 mm$^3$, and the pores of the porous vent 910 representing a volume of about 50 mm$^3$.

Needle assembly 410 may be assembled as follows. Fluid inlet cannula 436 is positioned through first end 414 of housing 412 such that the open interior end 439 is positioned within an interior portion of housing 412 at first portion 419 and patient puncture tip 438 extends externally of first end 414. Fluid outlet cannula 452 is positioned within housing 412 through the opposite end, such that open internal end 464 is positioned within an interior portion of housing 412 at first portion 419 adjacent interior end 439 of fluid inlet cannula 436, with a slight gap therebetween, and with non-patient puncture tip extending externally of second end 416. Fluid inlet cannula 436 and fluid outlet cannula 452 may be affixed therein in any known manner, desirably through a medical grade adhesive.

In alternate embodiments including only a single cannula 470, such cannula 470 is affixed within housing 412 such that opening 444 is positioned within the interior of housing 412 at first portion 419, with patient puncture tip 438 extending externally of first end 414 and non-patient puncture tip 462 extending externally of second end 416.

Porous vent 910 is then inserted within housing 412 and positioned over fluid outlet cannula 454 (or over the single cannula 470), and element 428 is thereafter affixed to the second end 416, enclosing the interior of housing 412. Sealable sleeve 461 is then affixed over protrusion 429. As such, the interior of housing 412 is closed from the external environment, with the sole path for fluid communication between the interior of housing 412 and the external environment being provided through the patient puncture tip 438.

Needle assembly 410 assembled as such can be used in connection with a blood collection tube holder 800, as depicted in the embodiment shown in FIGS. 12A and 12B. Such assembly may be accomplished through the rear open end of blood collection tube holder 800, so that the entire needle assembly 410 is inserted to a portion where at least patient puncture tip 438 and at least a portion of inlet cannula 436 extend out through the front end of blood collection tube holder 800. In embodiments where second portion 421 of needle assembly 410 is radially larger than first portion 419, such an insertion and arrangement enables the secondary chamber 427 to be fully contained within the internal space within collection tube holder 800, and with flashback chamber 426 extending out from a front end thereof.

In use, needle assembly 410 may be provided with collection tube holder 800 attached thereto. Patient puncture tip 438 is inserted through the skin of a patient and into the patient's vasculature, desirably into a vein. Upon venipucture, a closed environment is achieved within housing 412, since housing 412 is an entirely closed structure, and since sealable sleeve 461 closes off the only outlet of housing 412 (i.e., fluid outlet cannula 452). The patient's blood pressure causes blood to flow through patient puncture tip 438, into fluid inlet cannula 436, and out interior end 439 (or through opening 444 in the embodiment of FIGS. 12A and 12B), into flashback chamber 426 surrounding interior end 464 of outlet cannula 452. The transparent or translucent nature of housing 412 permits visualization of the blood within flashback chamber 426, providing an indication that venipuncture is achieved.

Since the interior of housing 412 is a closed environment, the flow of blood into flashback chamber 426 causes air to be trapped within the housing interior, including within flashback chamber 426, porous vent 910 and secondary chamber 427, as well as within fluid outlet cannula 452, causing such trapped air to be slightly pressurized therein. Flashback chamber 426 and secondary chamber 427 are configured through their size and dimensions such that the volumes thereof permit blood to flow into flashback chamber 426 at this initial venipucture, but the build up of air pressure within the pores of porous vent 910 and within secondary chamber 427 prevents blood from fully contacting porous vent 910, and desirably prevents blood from even partially contacting porous vent 910 at the initial venipuncture.

After such initial venipuncture and flash visualization, a sample collection container having a negative pressure therein, such as an evacuated blood collection tube (not shown) as is commonly known in the art, is inserted within the tube holder 800. The stopper (not shown) of such evacuated container contacts and displaces sealable sleeve 461, causing non-patient puncture tip 462 to puncture through sealable sleeve 461 and through the stopper of the evacuated container. At this point, fluid communication is established between the non-patient puncture tip 462 and the interior of the evacuated collection container. The negative pressure within the evacuated collection container draws the blood that has collected within flashback chamber 426 into fluid outlet cannula 452 and into the evacuated collection container. Along with the blood within flashback chamber 426, the negative pressure within the evacuated collection container will also draw at least a portion of the air out of the flashback chamber 426 and out of the secondary chamber 427 through the pores of porous vent 910, toward and into the evacuated collection container. In addition, the close proximity and alignment of fluid outlet cannula 452 and fluid inlet cannula 436 causes blood to be drawn from fluid inlet cannula 436 and from the patient, simultaneously with such air being drawn from the flashback chamber 426 and secondary chamber 427.

Such drawing of air reduces the pressure within the flashback chamber 426 and the secondary chamber 427, establishing a negative pressure therein with respect to the patient's bloodstream and with respect to the external environment. This negative pressure that has been established within the interior of housing 412, and specifically within flashback chamber 426 and secondary chamber 427, draws additional blood from within fluid inlet cannula 436 and from the patient into flashback chamber 426, with the blood contacting porous vent 910. With such blood filling flashback chamber 426, the blood fully contacts the surface of porous vent 910 that extends within flashback chamber 426, and begins to fill the pores of porous vent 910. Such filling of the pores of porous vent 910 that are directly at the interface of porous vent 910 and flashback chamber 426 closes off the porous vent from airflow therethrough, but does not fully act as a seal, in that the blood does not cause the material of the porous vent to swell or close off to air flow, but instead merely physically fills the voids within the porous vent. Moreover, since a portion of the air within secondary chamber 427 has been drawn out from secondary chamber 427, secondary chamber 427 represents a closed chamber with a negative pressure therein relative to the external environment. Since the volume of secondary chamber 427 represents a substantial portion of the overall interior volume of housing 412, a significant portion of interior volume of housing 412 downstream of the filled pores at the interface of porous vent 910 and flashback chamber 426 remains at a negative pressure with respect to the remainder of the interior volume. Secondary chamber 427 will therefore continue to have a drawing effect on the blood within the pores of porous vent 910 and within flashback chamber 426 through the pores of porous vent 910 toward secondary chamber 427, without releasing any air from the secondary chamber 427 in the opposite direction due to the pores of porous vent 910 at the interface of the flashback chamber 426 being filled with blood, thereby effectively preventing air flow through porous vent 910 due to the filled pores. The draw created by the negative pressure within secondary chamber 427 has a fluid resistance based on the blood filling the pores of porous vent 910 and based on the tortuous path created by the pores of porous vent 910, and therefore is a gradual draw with reduced fluid movement.

At this point, the evacuated collection container and the secondary chamber 427 are both at a negative pressure with respect to the external environment (and with respect to the patient's bloodstream), and therefore both effect a draw from the fluid inlet cannula 436. This mutual drawing effect may essentially establish an equilibrium within the flashback chamber 426, such that the blood contained within the flashback chamber 426 is not drawn toward or into either the secondary chamber 427 through the pores of porous vent 910 or into the evacuated collection container through the fluid inlet cannula 436, but instead essentially remains within flashback chamber 426 in a steady state. The negative pressure of the evacuated collection container draws blood directly from the patient through fluid inlet cannula 436, due to the close proximity and alignment of fluid outlet cannula 452 and fluid inlet cannula 436, as well as due to the equilibrium established within flashback chamber 426 (based on the opposite draw forces between the evacuated collection container and the evacuated secondary chamber 427). The continual draw of blood into the evacuated collection container gradually causes the pressure within the collection container to increase.

Once the evacuated collection container is filled with the desired amount of blood, the container is removed from the non-patient puncture tip 462, thereby releasing the fluid communication between the non-patient puncture tip 462 and the evacuated collection container, with sealable sleeve 461 then covering and closing off non-patient puncture tip 462. Absent such draw from the negative pressure of the evacuated collection tube, the negative pressure within the secondary chamber 427 effects a slight draw on the blood within flashback chamber 426 through the pores of porous vent 910. Such draw, however, is slow and gradual, due to the tortuous path of blood flow through the pores of porous vent 910.

Additional evacuated collection containers can thereafter be inserted into tube holder 800 and used for sample collection through non-patient puncture tip 462 as described above, by placing a second evacuated collection container within the holder 800 and establishing fluid communication between the non-patient puncture tip 462 and the interior of the evacuated collection container by puncturing the stopper, as discussed. In such further sampling, the evacuated collection container and the secondary chamber 427 are both at a negative pressure, and therefore both effect a draw from the fluid inlet cannula. As above, this effect essentially establishes an equilibrium within the flashback chamber 426, thereby preventing the blood contained within the flashback chamber 426 from being drawn toward or into either the secondary chamber 427 (through the porous vent 910). The negative pressure of the evacuated collection container draws blood directly from the patient through fluid inlet cannula 436 as discussed above, due to the close proximity and alignment of fluid outlet cannula 452 and fluid inlet cannula 436. Once any such additional evacuated collection containers are filled with the desired amount of blood, the container is removed from the non-patient puncture tip 462, thereby releasing the fluid communication between the non-patient puncture tip 462 and the evacuated collection container, with sealable sleeve 461 then covering and closing off non-patient puncture tip 462.

Once all of the desired blood samples have been drawn in this manner, patient puncture tip 438 is removed from the vasculature of the patient (i.e., from the bloodstream), thereby exposing the opening of patient puncture tip 438 to the external environment. Since the sole communication path between the housing interior and the external environment is through patient puncture tip 438, the negative pressure established within secondary chamber 427 relative to the external environment will affect a gradual draw on the blood contained within flashback chamber 426 and within fluid inlet cannula 436 toward and through porous vent 910. Such drawing effect will displace and move any blood contained within fluid inlet cannula 436 away from patient puncture tip 438, toward secondary chamber 427, thereby preventing any blood from leaking from patient puncture tip 438 out of fluid inlet cannula 436. Such negative pressure within secondary chamber 427 may continue to have a gradual drawing effect through the porous vent 910 for a prolonged period of time after removal of patient puncture tip 438 from the patient, and may draw all of the remaining blood contained within fluid inlet cannula 436 and flashback chamber 426 through porous vent 910 and/or into secondary chamber 427. Needle assembly 410 can then be properly disposed of in known manner.

Figure 13A:
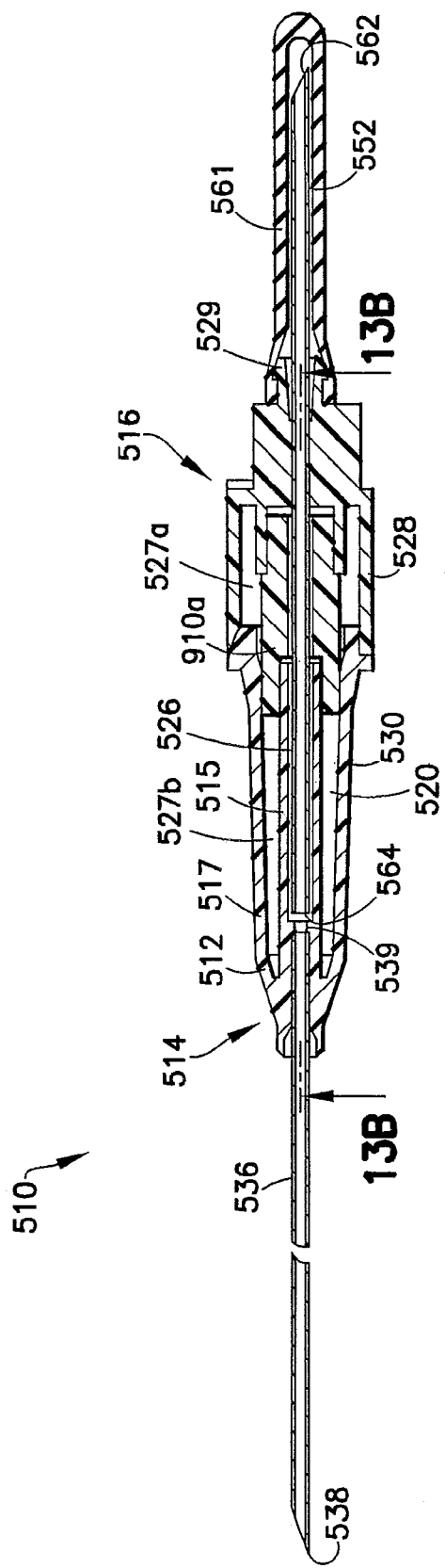
FIG. 13A is a cross-sectional view of a needle assembly having a flash chamber used in connection with a blood collection assembly in yet a further embodiment.
Figure 13B:
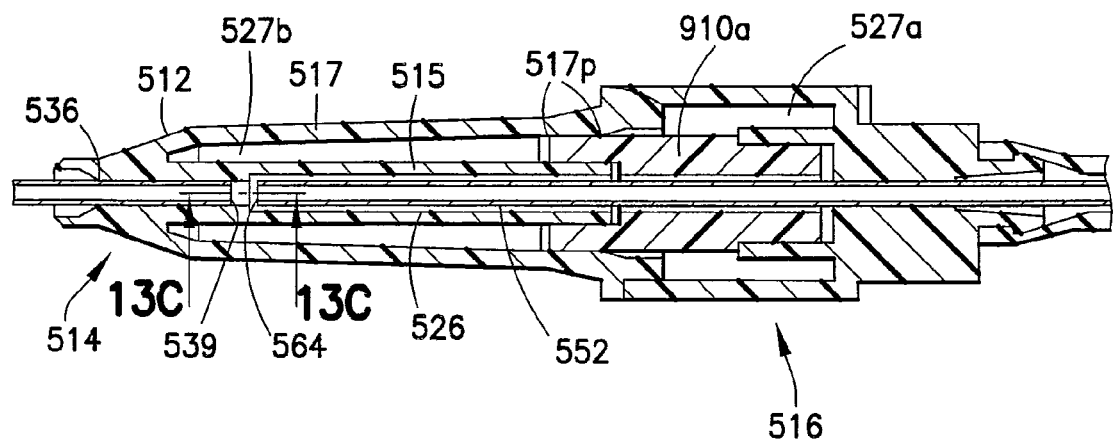
FIG. 13B is an enlarged sectional view of a portion of the needle assembly of FIG. 13A.
Figure 13C:
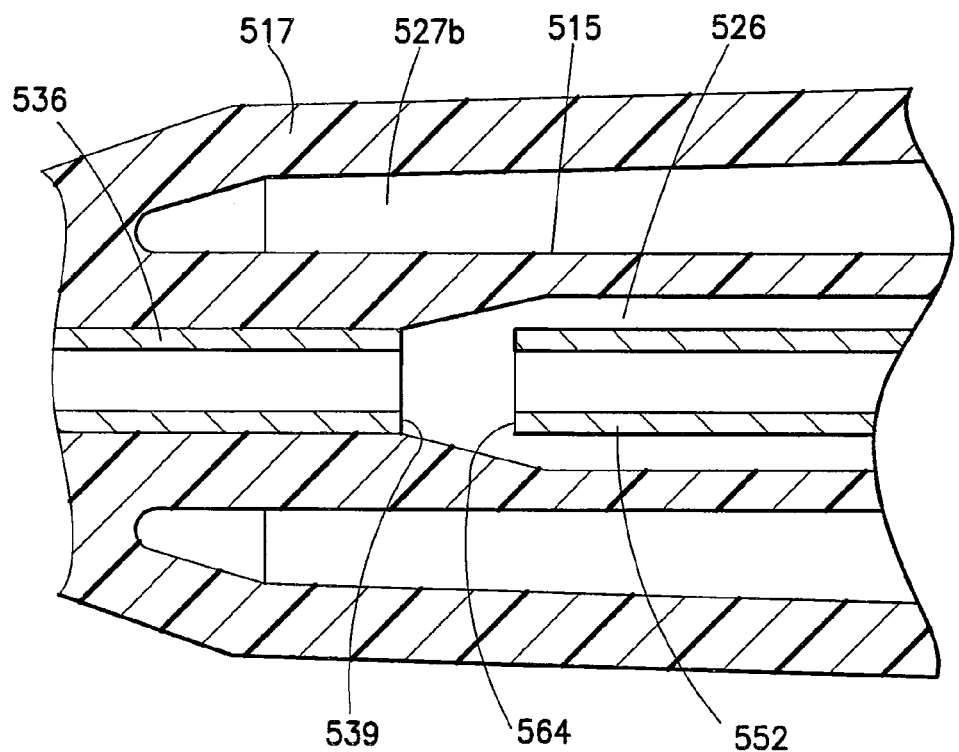
FIG. 13C is an enlarged sectional view of a portion of the needle assembly of FIG. 13B.

FIGS. 13A, 13B, and 13C depict yet a further embodiment of a needle assembly. The needle assembly shown in FIGS. 13A-13C is similar to the embodiment described above in connection with FIGS. 8-10, 11A, and 11B, albeit with the secondary chamber further comprising a plurality of interior regions that are in fluid communication with each other, and desirably gas venting fluid communication, to define the interior volume of the secondary chamber.

In particular, as depicted in FIG. 13A, needle assembly 510 includes a housing 512 having a fluid inlet end or first end 514 and a fluid outlet end or second end 516. Needle assembly 510 further includes a fluid inlet cannula 536 extending from first end 514 of housing 512. Fluid inlet cannula 536 extends between an exterior end that defines a first puncture tip such as a sharpened bevel at patient puncture tip 538, and an interior open end 539 extending within first end 514 of housing 512, and may be fixedly mounted therein. Fluid inlet cannula 536 is characterized further by a substantially cylindrical lumen extending between the ends and communicating with the interior of housing 512.

Needle assembly 510 also includes a second puncture tip such as non-patient puncture tip extending from second end 516 of housing 512, such as through a second cannula in the form of fluid outlet cannula 552. In particular, the end of fluid outlet cannula 552 may define a sharpened bevel forming non-patient puncture tip 562. Fluid outlet cannula 552 extends within second end 516 of housing 512, and may be fixedly mounted therein. Fluid outlet cannula 552 is characterized further by a substantially cylindrical lumen communicating with the interior of housing 512. Outlet cannula 552 is mounted within housing 512 so that an interior end 564 passes substantially coaxially therein such that outlet cannula 552 substantially aligns axially with the interior end of inlet cannula 536, in a similar manner as discussed in connection with the embodiment depicted in FIGS. 8-10, 11A, and 11B described above. For example, the interior end 564 of outlet cannula 552 may be spaced only a small distance from the interior end 539 of inlet cannula 536, thereby forming an axial gap therebetween for flow of blood into flashback chamber 526 about outlet cannula 552 as shown in FIG. 13C, or may be a single cannula having an opening therein, as described in connection with the embodiment of FIGS. 12A-12B.

As shown in FIGS. 13A-13C, needle assembly 510 includes a generally elongate longitudinal portion at first end 514, which generally includes an interior wall 515 and an exterior wall 517. Interior wall 515 extends generally longitudinally within housing 512, with a first diameter defining an interior chamber in the form of flashback chamber 526. Second end 516 defines a second portion having a second diameter that is generally larger than the first diameter of interior wall 515. Interior wall 515 is dimensioned to provide a radial gap around outlet cannula 552 of about 0.2 mm at an area surrounding the internal end 564 thereof, thereby achieving a substantially laminar blood flow within flashback chamber 526, as discussed above. Internal end 564 of outlet cannula 552 may be supported within housing 512, as in the embodiment discussed above. Needle assembly 510 may further include a sealable sleeve 561 mounted to fluid outlet end 516 of housing 512, such as through a mounting protrusion 529, as discussed above.

As with the embodiment of FIGS. 8-10, 11A, and 11B, needle assembly 510 further includes a porous vent 910a positioned within the interior of housing 512. Porous vent 910a is generally a cylindrically-shaped member with a central opening therein axially spaced from and encircling a portion of the cannula, particularly fluid outlet cannula 552. Porous vent 910a may be constructed of any suitable material as described above in connection with the embodiment of FIGS. 8-10, 11A, and 11B. Porous vent 910a is positioned within housing 512 in a manner such that housing 512 is divided into at least two distinct chambers, namely, a first chamber represented by flashback chamber 526 and a second chamber, representing the total internal volume of housing 512 that is positioned downstream of porous vent 910a. The term downstream is used herein to represent location with respect to the intended flow of blood through the housing 512 of needle assembly 510, i.e., blood flows through housing 512 from patient puncture tip 538 at fluid inlet cannula 536, through open end 539, into flashback chamber 526, into porous vent 910a, and toward the secondary chamber.

Porous vent 910a may be positioned within the interior of housing 512 at a location spanning the transition between the first end 514 and the second end 516. The interior volume of housing 512 is defined by the sum of the volumes of the flashback chamber and the secondary chamber as well as the volume represented by the pores of porous vent 910a. Such interior volume is configured so as to provide for certain attributes to the needle assembly 510, in particular with respect to the ability of the secondary chamber to be at least partially evacuated of a portion of the air therein to establish a negative pressure therein upon application of an evacuated tube to needle assembly 510 during use thereof, as described in connection with the embodiments set forth above. Such negative pressure within the secondary chamber draws blood into the pores of porous vent 910a based on when blood contacts porous vent 910a at the interface between the porous vent 910a and flashback chamber 526 and partially fills the pores thereof.

In the embodiment of FIGS. 13A-13C, the secondary chamber comprises a plurality of distinct interior regions, such as a first interior region 527a and a second interior region 527b. In particular, in the embodiment of FIGS. 8-10, 11A, and 11B, the secondary chamber 427 represents a radially enlarged portion at the second end 416 of housing 412, which enlarged portion accommodates the proper size of porous vent 910 and the proper internal volume required for secondary chamber 427 to function in the intended manner (i.e., to represent a substantial volume of the total interior volume of housing 512 so as to be able to establish a negative pressure therein during use, as described above). When used in connection with traditional blood collection needle assemblies, it is desirable to maintain a low profile for the assembly. This may be accomplished by providing for a reduced overall profile, and in particular an overall reduced diameter, of the secondary chamber.

In order to maintain the appropriate volume of the secondary chamber for the intended use, the secondary chamber may extend longitudinally along the housing 510. It is important, however, to ensure that sufficient volume exists between the secondary chamber and the pores of porous vent 910a in order to ensure a sufficient drawing effect once the secondary chamber is evacuated in its intended use. Accordingly, the secondary chamber may be divided into a plurality of regions, such as in the embodiment of FIGS. 13A-13C, in which the secondary chamber includes first interior region 527a and second interior region 527b, with first and second interior regions 527a, 527b in fluid communication with each other through porous vent 910a, and also in fluid communication with respect to flashback chamber 526 downstream of flashback chamber 526. In this manner, the total volume of the secondary chamber downstream of the flashback chamber, which is made up of a plurality of interior regions separated by the porous vent, is sufficient to achieve the intended use of the device as described herein, by maintaining the secondary chamber as a significant amount of the total volume of the needle housing.

While the present embodiment depicts two interior regions 527a and 527b, it is contemplated that the number of interior regions can be any number, so long as the total interior volume of the secondary chamber (represented by the total volume of the combined interior regions positioned downstream of porous vent 910a), define a downstream secondary chamber volume corresponding to the volume and ratios described above with respect to the embodiment of FIGS. 8-10, 11A, and 11B.

First interior region 527a of the secondary chamber may generally be located adjacent the second end 516 of housing 512, while second interior region 527b of the secondary chamber may be positioned generally concentric about a portion of the flashback chamber 526. This may be accomplished by providing housing 512 as a two-part housing, with first end 514 representing a main body portion 530 of the housing, and second end 516 representing a separate body portion 528 of the housing that is attachable to the main body portion 530, forming housing 512. For example, main body portion 530 of the housing may include interior wall 515 defining flashback chamber 526 and exterior wall 517 defining second interior region 527b. Main body portion 530 extends generally along the axis defining needle assembly 510 to define an elongate longitudinal portion, with interior wall 515 defining a first diameter for flashback chamber 526, and exterior wall 517 defining a second diameter for second interior region 527b. The exterior wall of separate body portion 528 at second end 516 of housing 512 generally defines the first interior region 527a, and exterior wall 517 of main body portion 530 of housing 512 generally defines second interior region 527b. In this manner, second interior region 527b extends distally from the porous vent 910a longitudinally and annularly surrounding a portion of flashback chamber 526. Desirably, both interior wall 515 and exterior wall 517 are transparent or translucent, such that the contents of flashback chamber 526 (such as blood flow therein) can be viewable through the second interior region 527b and/or through the first interior region 527a.

Exterior wall 517 of housing 512 may generally taper from a larger diameter to a smaller diameter toward first end 514. A portion of exterior wall 517 shown in FIG. 13B at portion 517p may include a substantially constant diameter for accommodating porous vent 910a therein in a tightly sealed arrangement. Alternatively, porous vent 910a may include dimensions that taper to coincide with the interior wall surface along tapering exterior wall 517.

Figure 15:
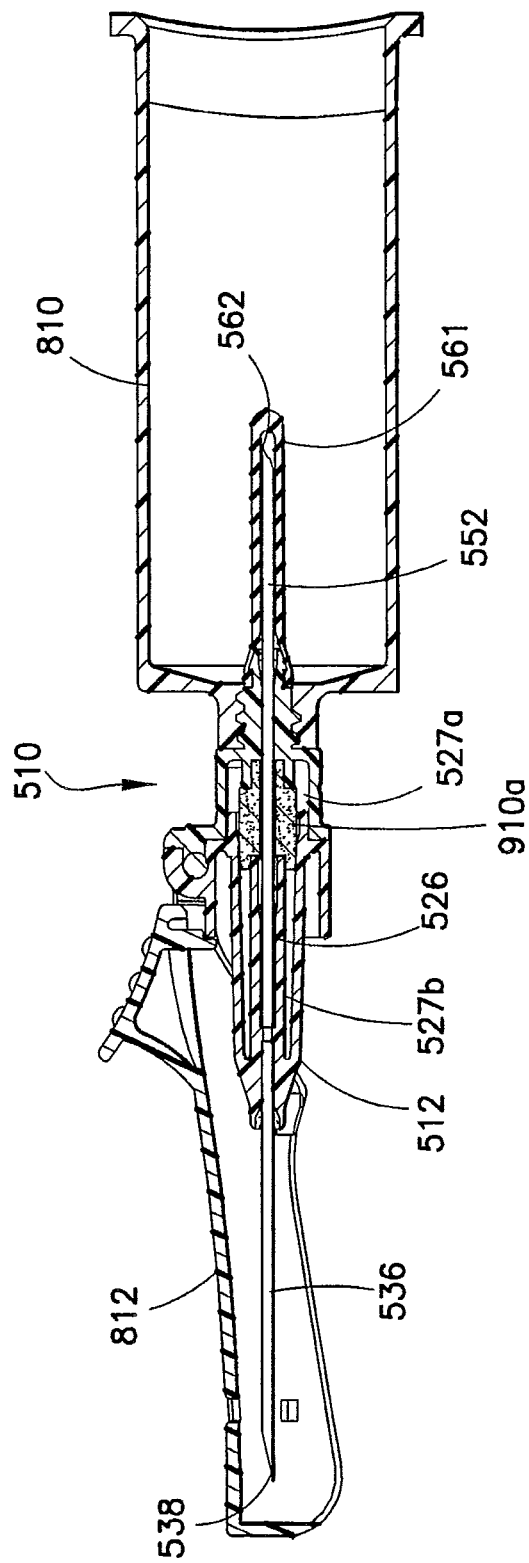
FIG. 15 is a side view of the needle assembly of FIG. 14.
Figure 16:
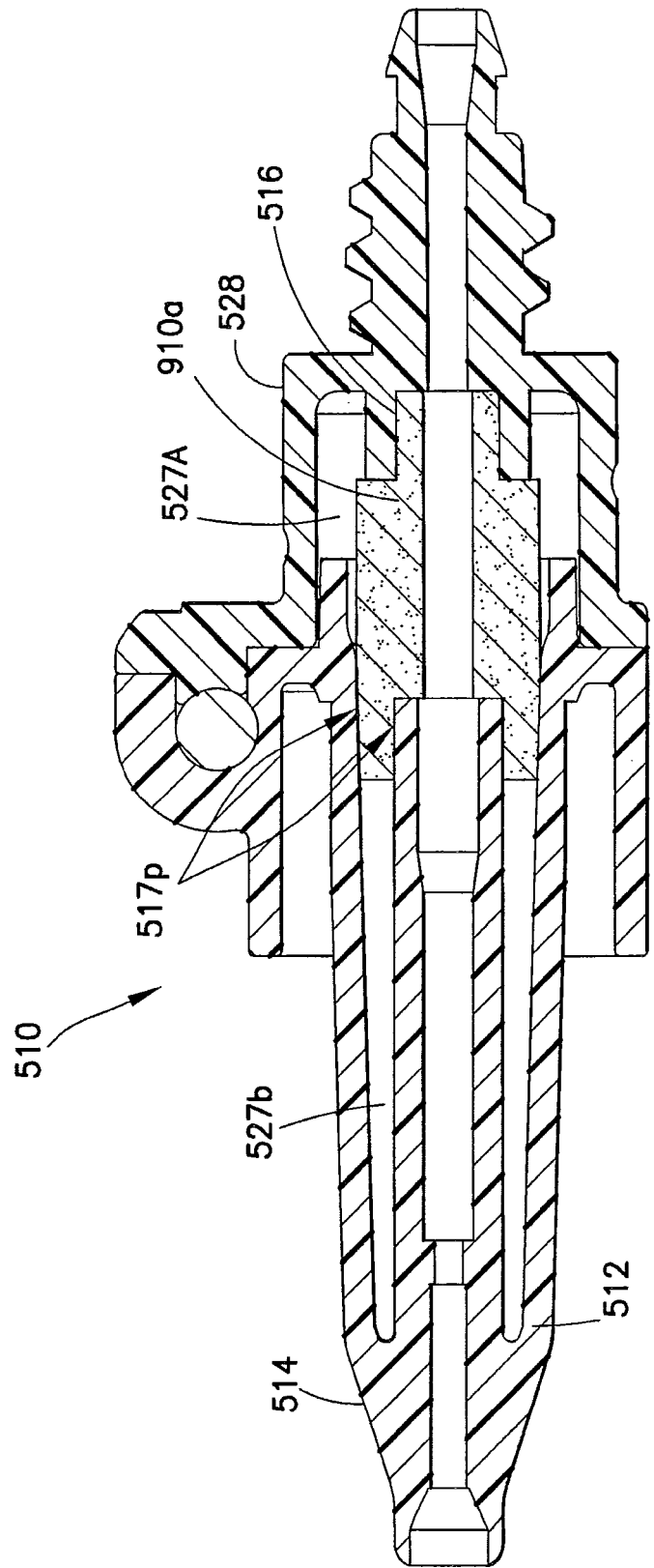
FIG. 16 is an enlarged side sectional view of the needle assembly of FIG. 15 without the cannula.

FIGS. 14-16 depict a further embodiment, in which needle assembly 510 is shown in use in connection with a safety blood collection needle assembly, including tube holder 810 for accommodating an evacuated blood collection tube (not shown) during a standard blood collection procedure in known manner, and a pivoting safety shield 812 for protecting the needle after use of the blood collection needle assembly.

In use, needle assembly 510 works in substantially the same manner as needle assembly 410 described above in connection with FIGS. 8-10, 11A, 11B, 12A, and 12B, with first and second interior regions 527a, 527b acting in the same manner as secondary chamber 427 described in the prior embodiment. In particular, needle assembly 510 is provided in combination with a tube holder, such as tube holder 810. Upon venipuncture of fluid inlet cannula 536 with a patient, blood flows into fluid inlet cannula 536 based on blood pressure of the patient and out the open end 539 thereof, into flashback chamber 526, such as shown in FIG. 13A, for visualization of blood flow, but does not fully contact the pores of porous vent 910a. After flash visualization, an evacuated blood collection container is inserted into tube holder 810 for piercing by the non-patient puncture tip 562 of fluid outlet cannula 552, which draws blood out from flashback chamber 526 and draws air out from first and second interior regions 527a, 527b, thereby reducing the pressure within flashback chamber 526 and first and second interior regions 527a, 527b, in a manner as described above. Thereafter, the negative pressure within flashback chamber 526 and first and second interior regions 527a, 527b draws blood from the patient through fluid inlet cannula 536, fully contacting the surface of porous vent 910a at the interface between porous vent 910a and flashback chamber 526 to fill the pores thereof. Since the interior volume within first and second interior regions 527a, 527b has been evacuated, first and second interior regions 527a, 527b represent a closed environment with a negative pressure therein, and therefore continue to have a drawing effect on the blood within the filled pores of porous vent 910a and within flashback chamber 526, as discussed above. Once all tubes are filled and removed, the negative pressure is maintained within first and second interior regions 527a, 527b due to the filled pores of porous vent 910a sealing off first and second interior regions 527a, 527b from the external environment, and such negative pressure within first and second interior regions 527a, 527b continues to affect a gradual draw on the blood contained within the pores of porous vent 910a and flashback chamber 526 and within fluid inlet cannula 536 away from patient puncture tip 538, thereby preventing any blood from leaking from patient puncture tip 538. Such continual draw may cause blood to flow completely through the pores of porous vent 910a and into one or both of first and second interior regions 527a, 527b.

Figure 17:
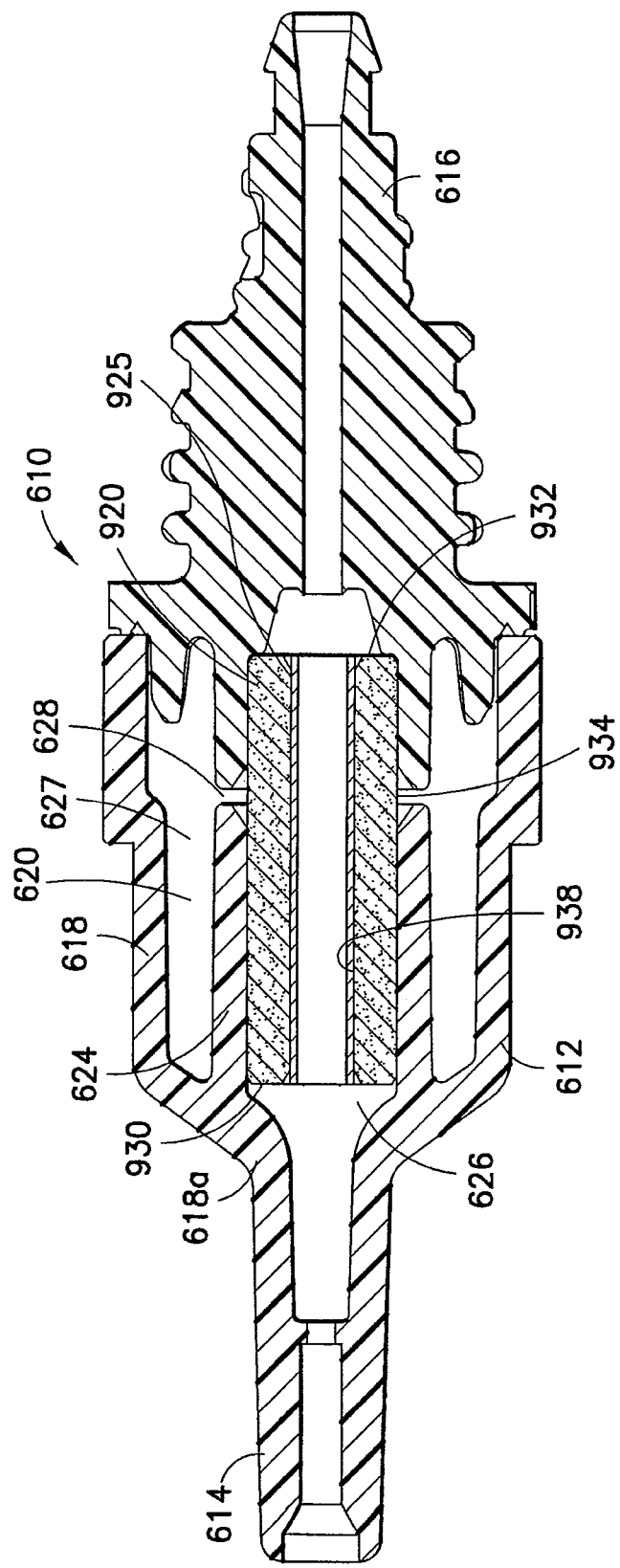
FIG. 17 shows a cross-sectional view of the needle assembly of the invention, without the cannula, according to one design including a blocking member located within the porous vent.
Figure 21:
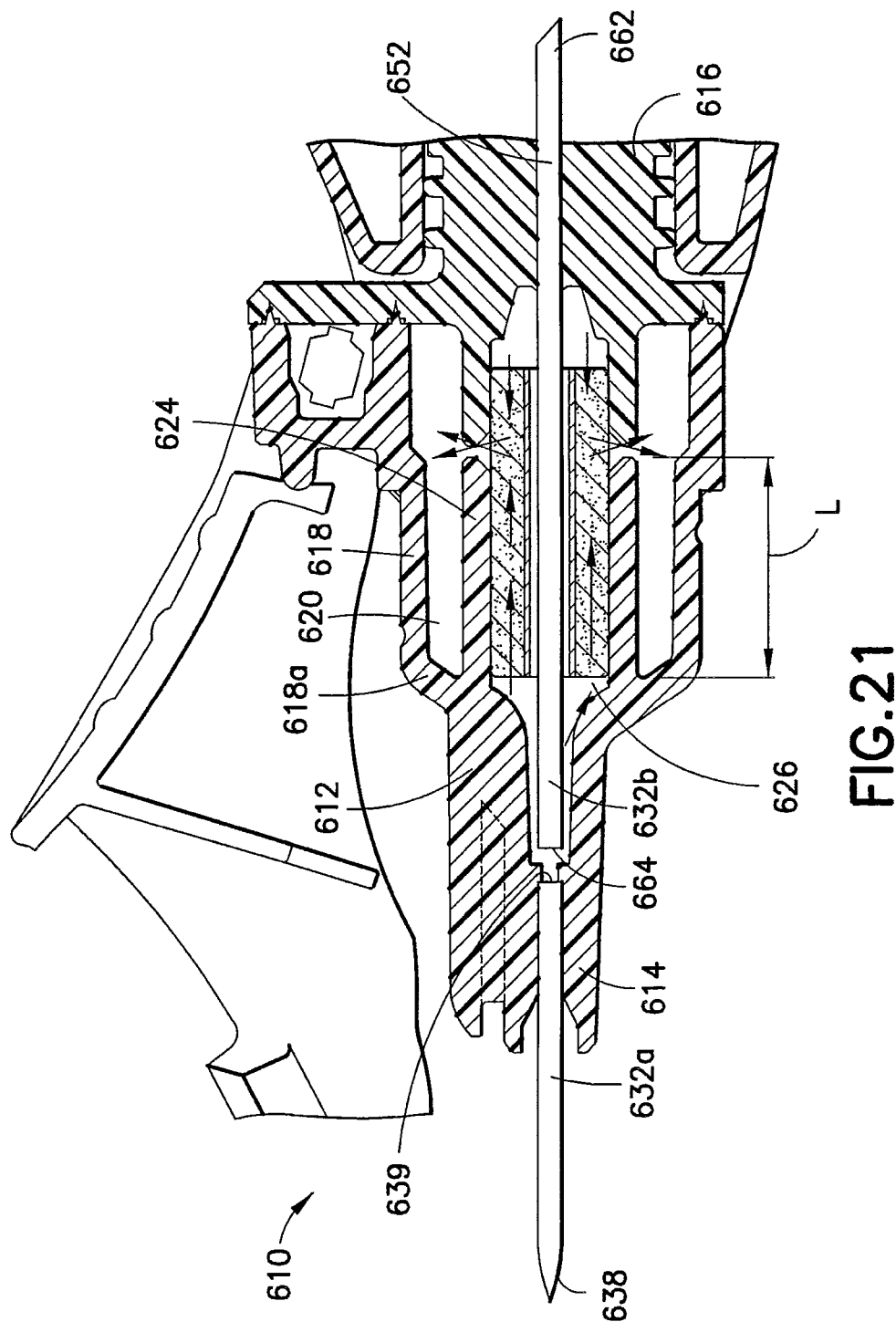
FIG. 21 is a cross-sectional view of the needle assembly of the invention including the blocking member of the invention and showing one embodiment of the controlled flow of fluid along the longest path through the porous vent wherein the longest path is in the longitudinal direction.

Reference is now made to FIGS. 17 and 21 which show a cross-sectional view of the needle assembly of the invention according to another design, generally indicated as 610, and having a porous vent 920 including a blocking member 925 located within the porous vent 920. According to this needle design, the needle assembly 610 includes a housing 612 defining a housing interior 620. The housing includes a first fluid inlet end 614, a second fluid outlet end 616, and an exterior wall 618 extending between the ends 614 and 616. The housing 612 includes a cylindrical interior wall 624 that extends in the housing interior 620. The exterior wall 618 includes a frusto-conical shaped portion 618a that extends toward the first fluid inlet end 614. This frusto-conical shaped portion 618*a*, the porous vent 920, and the cylindrical interior wall 624 define a flashback chamber or first chamber 626. The cylindrical interior wall 624, the exterior wall 618 of the housing, and a portion of the second fluid outlet end 616 define a second chamber 627. The first chamber 626 and the second chamber 627 are separated by a central aperture opening 628. The housing comprises at least one cannula 632*a*, 632*b*, as shown in FIG. 21 having a patient puncture tip 638 extending from a first end 614 of the housing 612 and a non-patient puncture tip 662 extending from a second end 616 of the housing 612. The non-patient puncture tip 662 and the patient puncture tip 638 are in fluid communication with each other within the housing interior 620.

Needle assembly 610 may be assembled according to one design as follows. Fluid inlet cannula 632 is positioned through first end 614 of housing 612 such that the open interior end 639 is positioned within an interior portion of housing 612 and patient puncture tip 638 extends externally of first end 614. Fluid outlet cannula 652 is positioned within housing 612 through the opposite end, such that open internal end 664 is positioned within an interior portion of housing 612 adjacent interior end 639 of fluid inlet cannula 632, with a slight gap therebetween, and with non-patient puncture tip extending externally of second end 616. Fluid inlet cannula 632 and fluid outlet cannula 652 may be affixed therein in any known manner, desirably through a medical grade adhesive.

This type of needle design assembly is also shown in FIGS. 13A-13C which shows a first fluid inlet cannula 536 extending from the housing 512, comprising the patient puncture tip 538 and a second fluid outlet cannula 552 extending from the housing 512, comprising the non-patient puncture tip 562. The first cannula 536 and the second cannula 552 are substantially axially aligned within the housing interior 520 and separated from each other by a gap between an interior end 539 of the first inlet cannula 536 and an interior end 564 of the second outlet cannula 552, the gap being in fluid communication with the first chamber 526 of the housing.

It can be appreciated that the alternative design, as discussed in relation to FIGS. 12A-12B can be used for the needle assembly shown in FIGS. 17 and 21 wherein only a single cannula is affixed within housing 612, such that an opening is positioned within the interior of housing 612, with patient puncture tip 638 extending externally of first end 614 and non-patient puncture tip 662 extending externally of second end 616.

The porous vent 920 is positioned within the housing interior 620 to separate the housing interior 620 into the first chamber 626 and the second chamber 627. The porous vent 920 includes pores for passage of fluid therethrough from the first chamber 626 to the second chamber 627 and the sole communication path between the housing interior 620 and the external environment is via the patient puncture tip 638.

Figure 18:
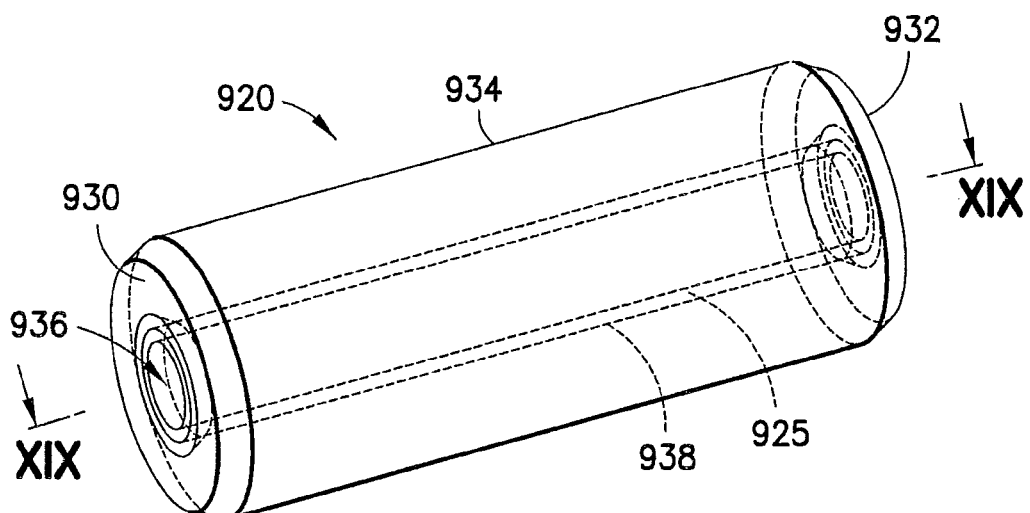
FIG. 18 shows a perspective view of the porous vent shown in FIG. 17.
Figure 19:
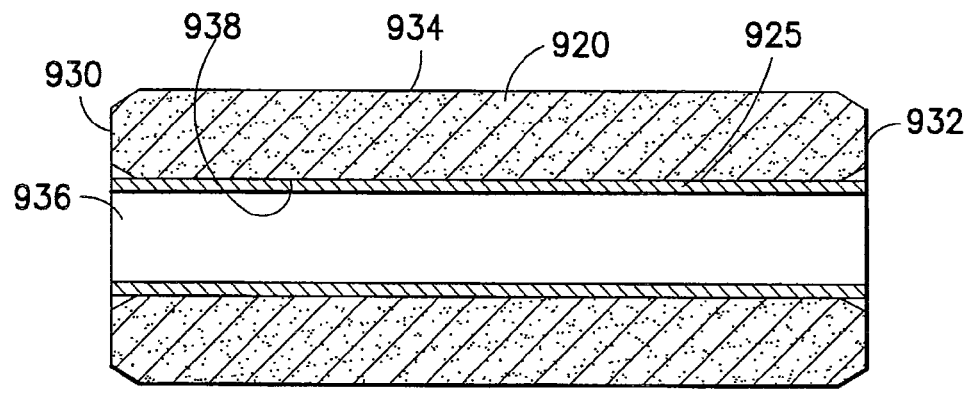
FIG. 19 shows a cross-section view of the porous vent taken along line XIX-XIX of FIG. 18.

The porous vent 920 of the present invention is configured to control flow of the fluid such that the fluid flows in an axial direction therethrough, as specifically shown in FIG. 21. The porous vent 920, as shown in FIGS. 18-19, comprises a tubular member having a first end face 930, a second end face 932, and a central portion 934 extending between the first end face 930 and the second end face 932. The tubular member includes an axial hole 936 configured for surrounding at least a portion 632*b* of the at least one cannula 632*a*, 632*b* and the blocking member 925 causes the fluid (air and blood) to flow along a controlled longitudinal path from the first end face 930 to the central portion 934 along a length L, as shown in FIG. 21, and/or to the second end face 932 of the porous vent 920 and, according to the design shown in FIGS. 17 and 21, through the central aperture opening 628 between the first chamber 626 and the second chamber 627 wherein the central aperture opening 628 is located adjacent to the central portion 934 of the porous vent 920.

Figure 20:
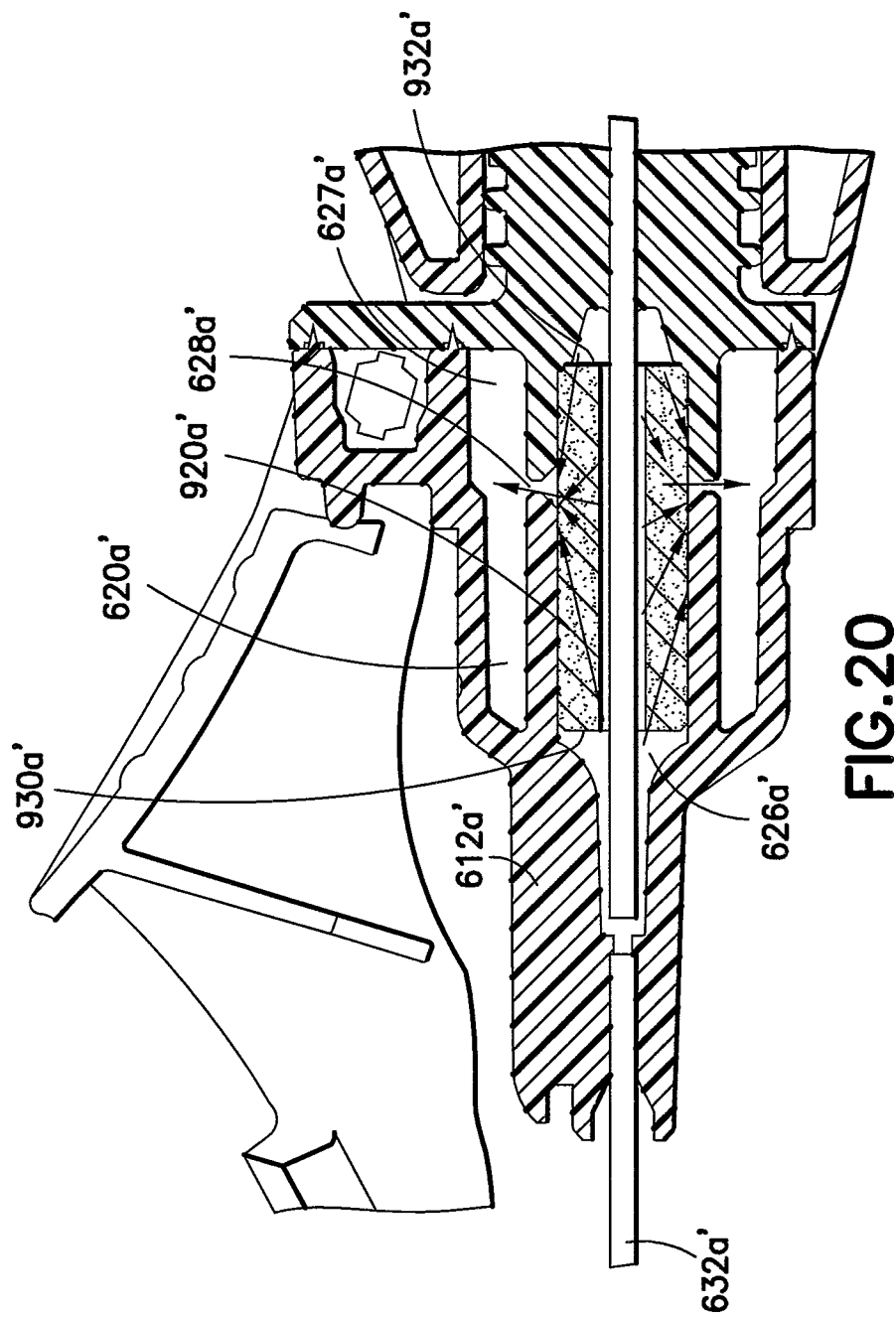
FIG. 20 is a cross-sectional view of the needle assembly using a porous vent without a blocking member showing the uncontrolled radial flow of fluid along the shortest path through the porous member.

As illustrated in FIG. 20, when using a porous vent 920*a*' without the blocking member 925 of the present invention, the fluid (air and blood) would enter into the porous vent 920*a*' through either or both of the first end face 930*a*' and/or a second end face 932*a*' of the porous vent 920*a*' and through the surface of the plug hole and flow outward through the porous media toward the second chamber 627*a*' along a plurality of radial paths in a random manner along the path of least resistance and subsequently through central aperture opening 628*a*' separating the first chamber 626*a*' from the second chamber 627*a*'. Alternatively, the fluid would flow at the seal interface with the plastic hub housings 612*a*'. The low resistance of the porous vent media 920*a*' can result in pooling of blood in the second chamber 627*a*' which depletes the differential pressure between the housing interior 620*a*' and the atmosphere. Consequently, this depleted differential pressure can result in a blood droplet being expelled from the patient puncture tip (not shown) when an evacuated tube is removed from the non-patient puncture tip (not shown) and the needle cannula 632*a*' is removed from the patient and exposed to atmospheric pressure due to the higher pressure being present in the hub.

The addition of the blocking member 925 to the inside diameter and/or along the axial bore 936 of the porous vent 920, according to the present invention and shown in FIGS. 18 and 19, prevents fluid from flowing radially along the shortest path from the inside diameter to the outside diameter of the porous vent 920. In particular, the present invention causes the fluid (blood and air) to flow axially or along the longest path through the porous vent 920, as shown in FIG. 21, through a controlled length of the porous media of the vent 920 from the end faces 930, 932 toward the central aperture opening 628 into the second chamber 627. The added blocking member 925 creates a longer and more tortuous path through the media which improves the fluid resistance and helps to retain differential vacuum in the second chamber 627.

Referring back to FIGS. 17-19, the blocking member 925 can comprise a bushing press-fitted into the inside surface 938 of the porous vent 920. According to one design, the bushing can be a stainless steel cannula cut to the length of the porous vent 920. One example can include a cut 17 gauge 302 stainless steel cannula press-fit as a bushing into the internal diameter of a sintered polyethylene cylindrical porous vent having a 7-12 micron pore size range. This particular arrangement has been found to have a slower decay of vacuum within the second chamber even after multiple tube draws, reduced pooling of blood into the second chamber, reduced bubbling in the flash chamber, and reduced blood droplet occurrences. Other examples of bushings include extruded plastic tubing and tubular molded parts. Other blocking members for 925 can include potting an annular space between the porous vent 920 and the at least one cannula 632 with an adhesive or sealant or blocking an end face 930, 932 of the porous vent 920 or any other location of the porous vent 920 to limit the flow path of fluid from the first chamber 626 to the second chamber 627 and maximize the tortuous flow length and vent resistance. According to yet another design, the blocking member 925 can be formed by melting or fusing a portion of the porous vent 920 on the inside surface portion 938 to render this portion non-porous. The melting or fusing of the vent 920 can be achieved by either heat or ultrasonic friction to the inside diameter portion 938 of the vent 920. According to still another design, the blocking member 925 can be a separate member, such as a plastic tubular member, that is placed in abutting relationship with respect to the inside surface 938 of the porous vent 920.

Referring back to FIGS. 12A-12B and previously discussed in relation to FIG. 21, the first and second cannulas 632, 652 can be replaced with a single cannula design. As shown in FIGS. 12A-12B, a single cannula 470 extends through the housing 412 wherein the single cannula 470 includes a lumen extending therethrough, a first end comprising the patient puncture tip, a second end comprising the non-patient puncture tip, and an opening 444 through the cannula 470 into the lumen at a location between the first end and the second end providing fluid communication between the lumen of the cannula 470 and the first chamber 426 of the housing.

With continuing reference to FIGS. 12A-12B, the porous vent 910 can be replaced with the porous vent 920 of the invention, including the blocking member 925, and can be used in this needle assembly 410. This needle assembly 410 has a housing design 412 wherein the first end 414 of the housing comprises an elongate longitudinal first portion 419 having a first diameter and the second end of the housing 416 comprises a second portion 421 having a second diameter larger than the first diameter of the first portion 419. In this manner, the first portion 419 of the housing 412 essentially defines the flashback or first chamber 426, and the second portion 421 of the housing 412 essentially defines the secondary chamber 427. The porous vent 920 of the invention may be positioned within the interior of housing 412 at a location spanning the transition between the first diameter of first portion 419 and the second diameter of second portion 421. The porous vent 920 including the blocking member 925 of the invention causes the fluid to flow along a controlled longitudinal path from the first end face 930 to one of the central location 934 and the second end face 932 and subsequently through a central aperture 428 opening between the first chamber 426 and the second chamber 427.

Figure 22C:
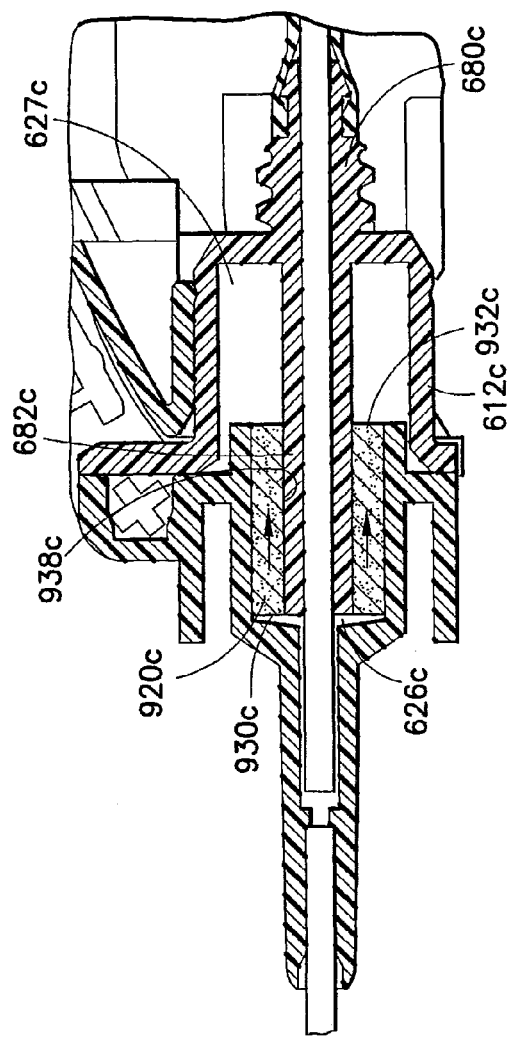
FIG. 22C shows a cross-sectional view of the needle assembly according to yet another design of the invention.
Figure 22D:
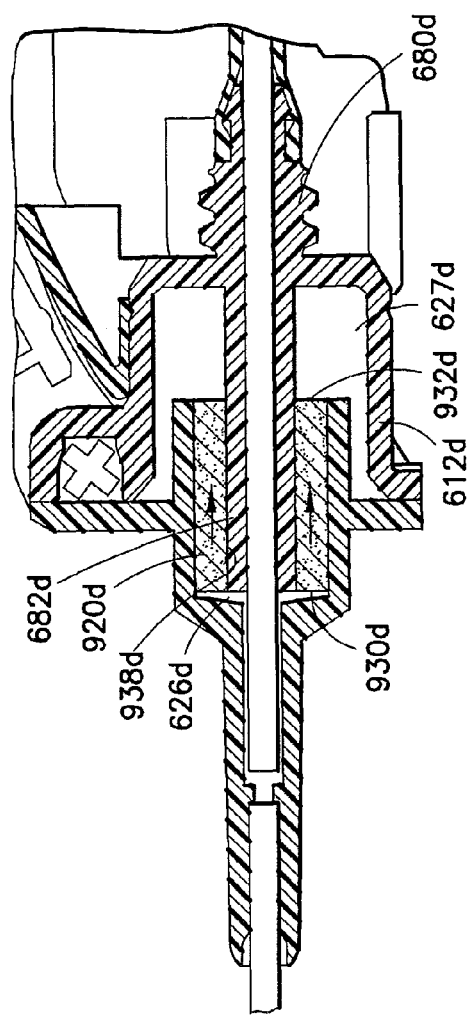
FIG. 22D shows a cross-sectional view of the needle assembly according to still another design of the invention.

Referring now to FIGS. 22A-22D, the porous vent 920a, 920b, 920c, and 920d, may be used in needle assemblies to separate the first chamber 626a, 626b, 626c, and 626d from the second chamber 627a, 627b, 627c, and 627d wherein the fluid flows through the first or second end face. In particular, as shown in FIG. 22A, the second end face 932a of the porous vent 920a is blocked such that fluid flows from the first chamber 626a to the back end of interior cylindrical wall 624a and from this second end face 932a, through the porous vent 920a and exits through the first end face 930a into the second chamber 627a. In FIG. 22A, the housing 612a includes a cylindrical interior wall portion 628a which extends into the axial hole of the porous vent 920a in an abutting relationship with respect to the inside surface 938a of the porous vent 920a. This cylindrical portion 628a functions as the blocking member to control the fluid flow within the porous vent 920a. In FIGS. 22B-22D, the fluid flows from the first end face 930b, 930c, 930d along a longitudinal path to the second end face 932b, 932c, 932d and exits through this second end face into the second chamber 627b, 627c, 627d.

In the designs shown in FIGS. 22B-22D, the housing 612b, 612c, 612d includes a rear hub 680b, 680c, 680d having a cylindrical portion 682b, 682c, 682d in an abutting relationship with respect to the inside surface 938b, 938c, 938d of the porous vent 920b, 920c, 920d. This cylindrical portion 682b, 682c, 682d functions as the blocking member to control the fluid flow within the porous vent 920b, 920c, 920d.

Figure 23B:
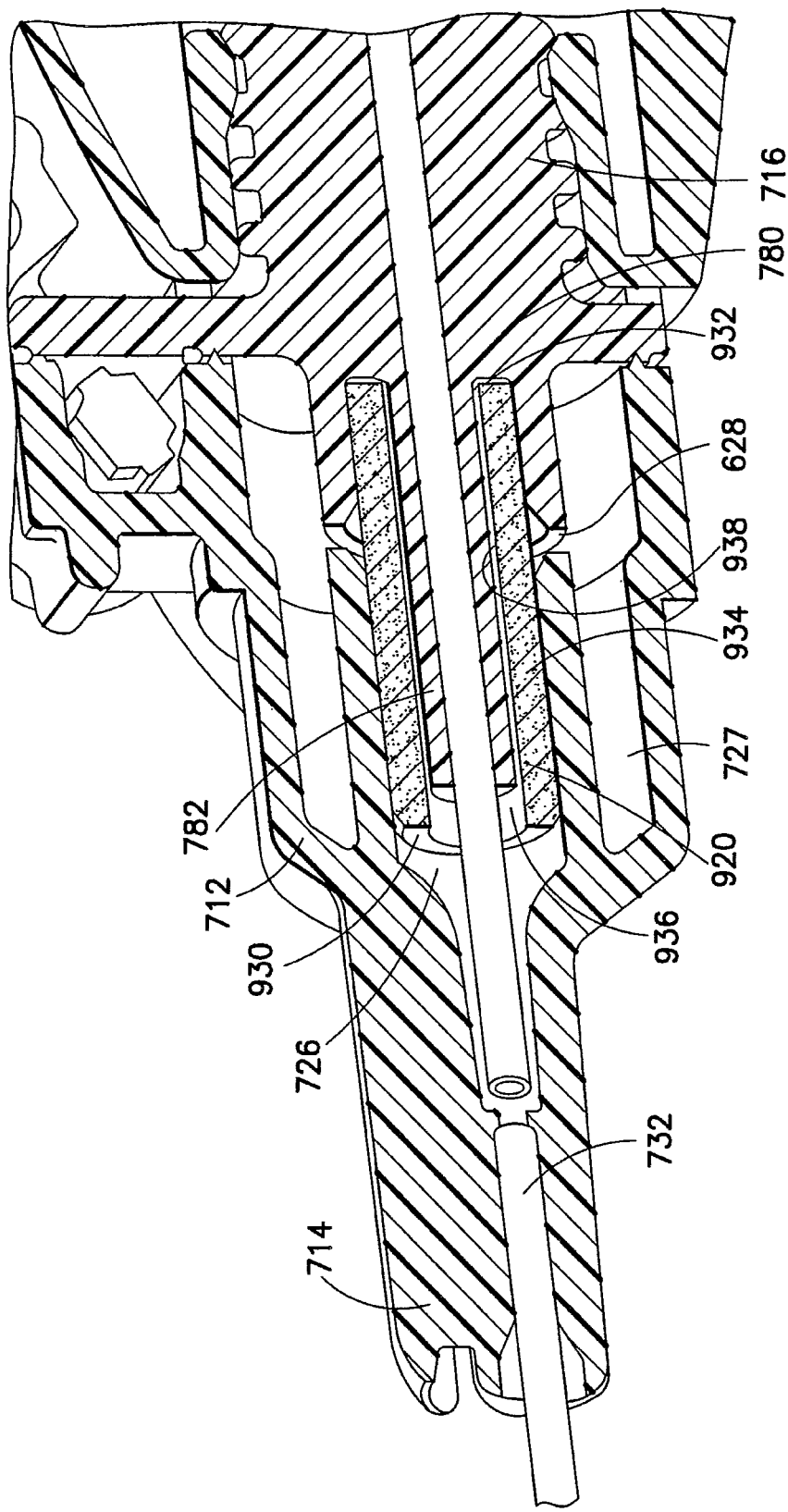
FIG. 23B shows a close-up cross-sectional perspective view of the porous vent and chamber arrangements of FIG. 23A.

Referring now to FIGS. 23A-23B there is shown a needle assembly, generally indicated as 710 comprising a housing 712 defining a housing interior 720. The housing comprises at least one cannula 732 having a patient puncture tip 738 extending from a first fluid inlet end 714 of the housing 712 and a non-patient puncture tip 762 extending from a second fluid outlet end 716 of the housing 712. The non-patient puncture tip 762 and the patient puncture tip 738 are in fluid communication with each other within the housing interior 720. The porous vent 920 is positioned within the housing interior 720 separating the housing interior into a first chamber 726 and a second chamber 727. The porous vent includes pores for passage of fluid therethrough from the first chamber 726 to the second chamber 727 and the porous vent 920 is configured to control flow of the fluid such that the fluid flows in an axial direction through the vent. In this design, the housing 712 includes a rear hub 780 having a cylindrical portion 782 extending therefrom and into the first chamber 726 toward the first end 714 of the housing 712 to define a portion of the first chamber 726. The sole communication path between the housing interior 720 and the external environment is via the patient puncture tip 738. As discussed in detail above, the porous vent 920 comprises a tubular member having a first end face 930, a second end face 932, and a central portion 934 extending between the first end face 930 and the second end face 932. The tubular member includes an axial hole 936, as shown in FIGS. 18, 19, and 23B, configured for surrounding at least a portion of the cylindrical portion 782 extending from the rear hub 780. The at least one cannula 732 is located within at least a portion of the cylindrical portion 782. The cylindrical portion 782 extends into the porous vent 920 and abuts against the inside surface 938, as shown in FIGS. 18, 19, and 23B, of the porous vent 920. This cylindrical portion 782 functions as the blocking member 925 to control the flow of fluid such that it flows along a controlled longitudinal path and subsequently through a central aperture opening 628 between the first chamber 726 and the second chamber 727. In the design shown in FIGS. 23A-23B, the rear hub 780 and the cylindrical portion 782 extending therefrom also block the second end face 932 of the porous vent 920 to prevent fluid flow through the second end face 932.

Figure 24:
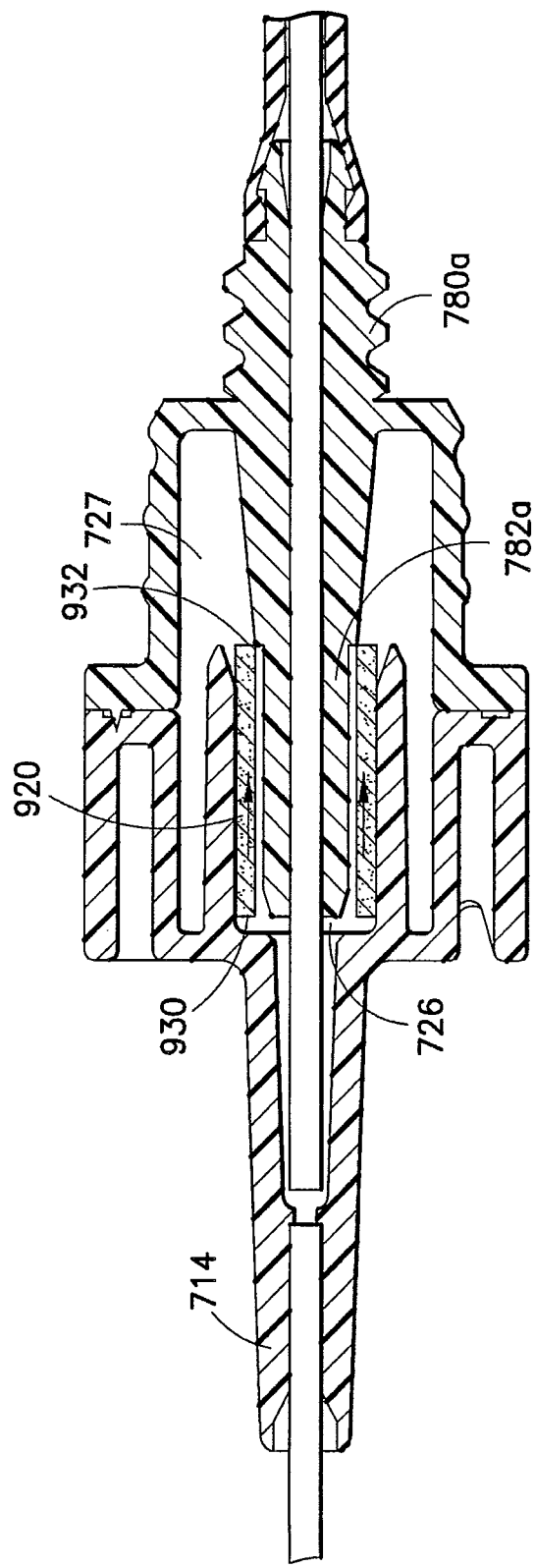
FIG. 24 shows a cross-sectional view of the needle assembly of the invention according to another design.

According to an alternative design, as shown in FIG. 24, the rear hub 780a can include a tapered cylindrical member 782a which extends into the first chamber 726 toward the first end 714 of the housing 712 to define a portion of the first chamber 726. Fluid, in the form of liquid and air enters into the porous vent 920 from the first end face 930, flows along a longitudinal path therethrough due to the presence of blocking member 925, and exits into the second chamber 727 through the second end face 932.

It can be appreciated that the needle assemblies shown in FIGS. 22A-22D, 23A-23B, and 24 can be used with the single cannula design, as described above in relation to FIGS. 12A-12B, or with a pair of cannulas including a gap between the interior blunt ends as described above in relation to FIGS. 13A-13C.

The blocking member 925 can be formed from a variety of methods and/or devices as discussed in detail above, such as from a bushing press-fitted into the inside surface of the porous vent, an adhesive located between an inside surface of the porous vent and an outer diameter surface of the cylindrical member 782, 782a, a fused inner surface portion of the porous vent 920, a separate member, such as a plastic member or a wall portion of the housing in abutting relationship with respect to the inside surface of the porous vent, or any other previously disclosed techniques for rendering a portion of the porous vent non-porous to control the axial flow of the fluid therethrough and to reduce random radial movement of the fluid.

The porous vent and blocking member of the present invention causing the fluid to flow along a controlled path through the porous vent along the longest path, depending upon the shape of the porous vent, results in slower decay of vacuum within the second chamber of the needle assembly even after multiple tube draws, reduced pooling of blood into the second chamber, and reduced blood droplet occurrences.

Figure 25:
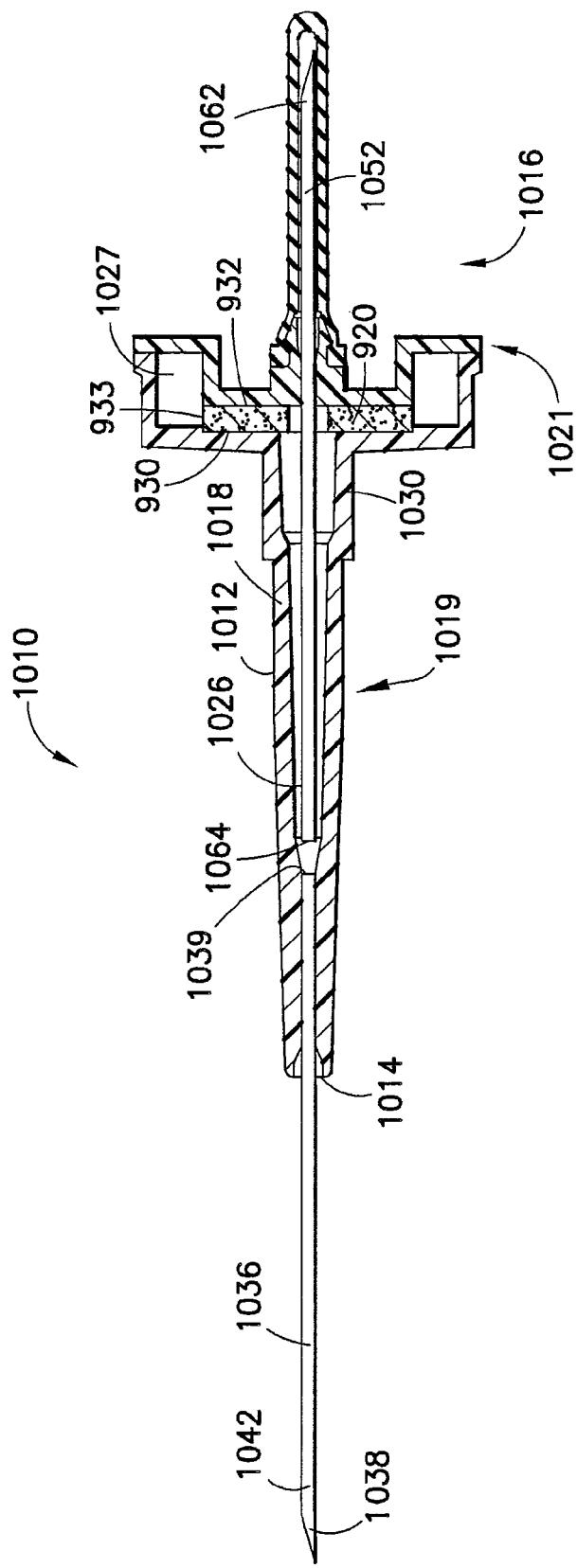
FIG. 25 is a cross-sectional view of the needle assembly of the invention including the blocking member of the invention and showing another embodiment of the controlled flow of fluid along the longest path through the porous vent wherein the longest path is in a radial direction.

FIG. 25 shows a cross-sectional view of the needle assembly of the invention including the blocking member of the invention and showing another embodiment of the controlled flow of fluid along the longest path through the porous vent 920 wherein the longest path is in a radial direction. The needle assembly, generally indicated as 1010, includes a housing 1012 having a fluid inlet end or first end 1014 and a fluid outlet end or second end 1016. Needle assembly 1010 includes exterior wall 1018 defining the housing interior. Exterior wall 1018 extends generally longitudinally at the first end 1014 forming an elongate longitudinal first portion 1019 having a first diameter. At second end 1016, exterior wall 1018 forms a second portion 1021 that has a second diameter that is generally larger than the first diameter of the first portion 1019. First portion 1019 and second portion 1021 may be arranged relative to each other in a variety of arrangements, so long as they are capable of functioning for transport of air therebetween as discussed herein. Needle assembly 1010 further includes a fluid inlet cannula 1036 extending from first end 1014 of housing 1012. Fluid inlet cannula 1036 includes an exterior end 1042 that defines a first puncture tip such as a sharpened bevel at patient puncture tip 1038, and extends within first end 1014 of housing 1012 and may be fixedly mounted therein. Fluid inlet cannula 1036 is characterized further by a substantially cylindrical lumen extending between the ends and communicating with the interior of housing 1012.

Needle assembly 1010 also includes a second puncture tip such as non-patient puncture tip 1062 extending from second end 1016 of housing 1012. Fluid outlet cannula 1052 extends within second end 1016 of housing 1012, and may be fixedly mounted therein. Fluid outlet cannula 1052 is characterized further by a substantially cylindrical lumen communicating with the interior of housing 1012. Outlet cannula 1052 is mounted within housing 1012 so that an interior end 1064 passes substantially coaxially therein such that outlet cannula 1052 substantially aligns axially with the interior end of inlet cannula 1036. The interior end 1064 of outlet cannula 1052 is spaced only a small distance from the interior end 1039 of inlet cannula 1036, thereby forming an axial gap therebetween for flow of blood into flashback chamber 1026 about outlet cannula 1052.

The porous vent 920 of FIG. 25 is washer-shaped, such that the longest path extends in the radial direction. The first face 930 and second face 932 of porous vent 920 are arranged to abut inside surfaces of first portion 1019 and second portion 1021. The first portion 1019 and second portion 1021 abutting the porous vent function as the blocking member to control the flow of the fluid (blood and air) such that it moves along the longest path, which is in a controlled radial direction from an inner portion of the porous vent to the outer circumferential end surface 933 of the porous vent 920, and out into secondary chamber 1027.

The relative dimensional calculations, volumes and pressures apply to both illustrated and unillustrated embodiments of the invention. Accordingly, the scope of the invention as defined by the appending claims is not limited to the specific illustrated embodiments. Various other changes and modifications may be effected therein by one skilled in the art without departing from the scope or spirit of the invention, and it is intended to claim all such changes and modifications as fall within the scope of the invention.

What is claimed is:

1. A needle assembly comprising:
   a housing defining a housing interior, said housing comprising at least one cannula having a patient puncture tip extending from a first end of the housing and a non-patient puncture tip extending from a second end of the housing, the non-patient puncture tip and the patient puncture tip being in fluid communication with each other within the housing interior; and
   a porous vent positioned within the housing interior separating the housing interior into a first chamber and a second chamber, the porous vent including pores for passage of fluid therethrough from the first chamber to the second chamber, said porous vent including a blocking member to control the flow of the fluid through the porous vent,
   wherein the sole communication path between the housing interior and the external environment is via the patient puncture tip.

2. The needle assembly of claim 1, wherein the porous vent is configured to reduce the flow of fluid along the shorter and least resistant paths through the porous vent.

3. The needle assembly of claim 1, wherein the porous vent comprises a tubular member having a first end face, a second end face, and a central portion extending between the first end face and the second end face, the tubular member having an axial hole configured for surrounding at least a portion of the at least one cannula.

4. The needle assembly of claim 3, wherein the porous vent is configured to cause said fluid to flow along a controlled longitudinal path from the first end face to one of the central portion and the second end face of the porous vent and through a central opening between the first and the second chamber wherein said central opening is located adjacent to said central portion of the porous vent.

5. The needle assembly of claim 1, wherein the porous vent comprises a tubular member having a first end face and a second end face, the tubular member having an axial hole configured for surrounding at least a portion of the at least one cannula and wherein the porous vent is configured to cause said fluid to flow along a controlled longitudinal path from the first end face to the second end face and into the second chamber through one of the first end face and/or the second end face.

6. The needle assembly of claim 1, wherein the porous vent is configured to cause said fluid to flow along a controlled radial path from the first chamber and an inner surface of the porous vent and out through a circumferential end surface of the porous vent into the second chamber.

7. The needle assembly of claim 1, wherein the blocking member is configured to block at least a portion of the porous vent to render this portion of the vent non-porous to control the flow of fluid therethrough.

8. The needle assembly of claim 7, wherein the blocking member is positioned to block at least a portion of an inside surface of the axial hole surrounding the at least a portion of the cannula.

9. The needle assembly of claim 8, wherein the blocking member comprises a bushing press-fitted into the inside surface of the porous vent.

10. The needle assembly of claim 9, wherein the bushing comprises one of a steel cannula, an extruded plastic tube, and a tubular molded part and wherein the bushing has a length equal to a length of the porous vent.

11. The needle assembly of claim 8, wherein the blocking member comprises one of an adhesive or sealant located between an inside surface of the porous vent and an outer diameter of the cannula or a member abutted against the inside surface of the porous vent.

12. The needle assembly of claim 11, wherein an end surface of the porous member or a central portion of the porous member is blocked with an adhesive material to control the flow of fluid through the porous vent.

13. The needle assembly of claim 8, wherein the blocking member comprises a melted or fused inner surface portion of the porous vent.

14. The needle assembly of claim 1, wherein the at least one cannula comprises a single cannula extending through the housing, said single cannula including a lumen extending therethrough, a first end comprising the patient puncture tip, a second end comprising the non-patient puncture tip, and an opening through the cannula into the lumen at a location between the first end and the second end providing fluid communication between the lumen of the cannula and the first chamber of the housing.

15. The needle assembly of claim 1, wherein the at least one cannula comprises a first cannula extending from the housing and comprising the patient puncture tip, and a second cannula extending from the housing and comprising the non-patient puncture tip, the first cannula and the second cannula being axially aligned within said housing interior and separated from each other by a gap in fluid communication with the first chamber of the housing.

16. The needle assembly of claim 1, wherein the first chamber and the second chamber are configured, such that upon insertion of the patient puncture tip into a patient, to cause blood to flow into the first chamber without sealing the porous vent, and upon application of a negative pressure source to said non-patient puncture tip, blood and air are drawn from said first chamber and air is drawn from said second chamber, thereby establishing a negative pressure within said second chamber with respect to an external environment of the needle assembly.

17. The needle assembly of claim 16, wherein upon removal of the patient puncture tip from the patient, the negative pressure within the second chamber prevents blood droplets from being present at the patient puncture tip.

18. A needle assembly comprising:
a housing defining a housing interior, said housing comprising at least one cannula having a patient puncture tip extending from a first end of the housing and a non-patient puncture tip extending from a second end of the housing, the non-patient puncture tip and the patient puncture tip being in fluid communication with each other within the housing interior; and
a porous vent positioned within the housing interior to separate the housing interior into a first chamber and a second chamber, the porous vent including pores for passage of fluid therethrough from the first chamber to the second chamber and a blocking member to control flow of the fluid through the porous vent such that the fluid flows in an axial direction through the porous vent,
wherein the sole communication path between the housing interior and the external environment is via the patient puncture tip, and
wherein the first end of the housing comprises an elongate longitudinal first portion having a first diameter and the second end of the housing comprises a second portion having a second diameter larger than the first diameter of the first portion.

19. The needle assembly of claim 18, wherein the porous vent is positioned within the housing interior between the first portion having a first diameter and the second portion having a second diameter at a location spanning a transition point between the first diameter of the first position and the second diameter of the second position.

20. The needle assembly of claim 19, wherein the porous vent comprises a tubular member having a first end face, a second end face, and a central portion located between the first end face and the second end face, the tubular member further including an axial hole configured for surrounding at least a portion of the cannula, said axial hole defining an inside surface, the blocking member being located at the inside surface of the axial hole for blocking at least a portion of the porous vent to render this portion of the vent non-porous to cause the fluid to flow along a controlled longitudinal path from the first end face to one of the central location and the second end face and subsequently through a central aperture opening between the first chamber and the second chamber.

21. The needle assembly of claim 20, wherein the blocking member is selected from the group consisting of a bushing press-fit into the inside surface of the porous vent; an adhesive or sealant located between an inside surface of the porous vent and an outer diameter of the cannula; a fused inner surface portion of the porous vent; and a member positioned adjacent to the inside surface of the porous vent.

22. A method of preventing leakage of blood from a patient needle tip in a needle assembly comprising:
a) receiving blood through a patient puncture tip and into a first chamber of a needle assembly, the needle assembly comprising:
  i) a needle housing defining a housing interior, said housing comprising at least one cannula having a patient puncture tip extending from a first end of the housing and a non-patient puncture tip extending from a second end of the housing; and
  ii) a porous vent positioned within the housing interior and separating the housing interior into a first chamber and a second chamber, with the non-patient puncture tip and the patient puncture tip being in fluid communication with each other within the first chamber such that the sole communication path between the housing interior and the external environment is via the patient puncture tip, the porous vent including pores for passage of blood and air therethrough from the first chamber into the second chamber, said porous vent including a blocking member to control flow of the blood and air through the porous vent;
b) establishing fluid communication between the non-patient puncture tip and a negative pressure source such that blood contained within the first chamber is drawn out of the non-patient puncture tip and air is drawn out of the second chamber through the porous vent, thereby establishing a negative pressure within the second chamber relative to the external environment of the needle assembly such that blood flows through the cannula into the first chamber and contacts the porous vent; and
c) drawing blood and air through the pores of the porous vent toward the second chamber based upon the negative pressure established within the second chamber such that blood contained within a lumen of the patient puncture tip is displaced away from the patient puncture tip and toward the second chamber to prevent blood droplets from being present at the patient puncture tip.

23. The method of claim 22, wherein the receiving step a) comprises receiving blood through the lumen of the patient puncture tip from a patient's bloodstream, and the drawing step c) displaces blood away from the patient puncture tip after removing the patient puncture tip from the patient's bloodstream.

24. The method of claim 22, including a further step after step b) and prior to step c) comprising releasing the fluid communication between the non-patient puncture tip and the negative pressure source.

25. The method of claim 22 wherein the porous vent comprises a tubular member having a first end face and a second end face, the tubular member further including an axial hole configured for surrounding at least a portion of the cannula, said method including rendering the inside surface of the axial hole non-porous to cause the fluid to flow along a controlled longitudinal path through the porous vent and subsequently into the second chamber.

26. The method of claim 22, wherein the porous vent is configured to cause said fluid to flow along a controlled radial path from the first chamber and an inner surface of the porous vent and out through a circumferential end surface of the porous vent into the second chamber.

27. The method of claim 24, including positioning said blocking member within the inside surface of the axial hole to render this inside surface non-porous.

28. The method of claim 27, wherein the blocking member is selected from the group consisting of a bushing press-fitted into the inside surface of the porous vent, an adhesive or sealant located between an inside surface of the porous vent, an outer diameter of the cannula, a fused inner surface portion of the porous vent, and a separate member positioned adjacent the inside surface of the porous vent.

29. A needle assembly comprising:
a housing defining a housing interior, said housing comprising at least one cannula having a patient puncture tip extending from a first end of the housing and a non-patient puncture tip extending from a second end of the housing, the non-patient puncture tip and the patient puncture tip being in fluid communication with each other within the housing interior;
a porous vent including an axial bore positioned within the housing interior separating the housing interior into a first chamber and a second chamber wherein the axial bore surrounds at least a portion of the at least one cannula, the porous vent including pores for passage of fluid therethrough from the first chamber to the second chamber; and
a blocking member located adjacent to or within the axial bore of said porous vent, said blocking member configured to control flow of the fluid such that the fluid flows in an axial direction along a longitudinal path through the porous vent,
wherein the sole communication path between the housing interior and the external environment is via the patient puncture tip.

30. The needle assembly of claim 29, wherein the blocking member is selected from the group consisting of a bushing press-fitted into the inside surface of the porous vent, an adhesive located between an inside surface of the porous vent and an outer diameter of the cannula, a fused inner surface portion of the porous vent, and a member positioned adjacent the inside surface of the porous vent.

31. The needle assembly of claim 29, wherein the blocking member comprises a bushing press-fitted within the axial bore of the porous vent and wherein the bushing is formed from a material selected from the group consisting of metal, plastic, composite, and a combination thereof.

32. The needle assembly of claim 29, wherein the blocking member comprises a cylindrical member extending from a portion of the housing into the porous vent and adjacent to the inside surface of the porous vent.

* * * * *